US012721639B2

(12) United States Patent
Zakhary et al.

(10) Patent No.: US 12,721,639 B2
(45) Date of Patent: Sep. 1, 2026

(54) INTRAOSSEOUS SLIDING OSTEOTOMY SYSTEM AND METHOD

(71) Applicant: WRIGHT MEDICAL TECHNOLOGY, INC., Memphis, TN (US)

(72) Inventors: Beniamin Zakhary, Marietta, GA (US); Louis Monaco, Salt Lake City, UT (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 54 days.

(21) Appl. No.: 18/893,044

(22) Filed: Sep. 23, 2024

(65) Prior Publication Data

US 2025/0009370 A1 Jan. 9, 2025

Related U.S. Application Data

(63) Continuation of application No. 17/814,889, filed on Jul. 26, 2022, now Pat. No. 12,121,246, which is a continuation of application No. 16/546,628, filed on Aug. 21, 2019, now Pat. No. 11,426,185.

(60) Provisional application No. 62/774,373, filed on Dec. 3, 2018.

(51) Int. Cl.
*A61B 17/17* (2006.01)
*A61B 17/16* (2006.01)

(52) U.S. Cl.
CPC ...... *A61B 17/1775* (2016.11); *A61B 17/1682* (2013.01)

(58) Field of Classification Search
CPC ........................ A61B 17/1775; A61B 17/1682
See application file for complete search history.

(56) References Cited

U.S. PATENT DOCUMENTS 6,926,720 B2 8/2005 Castaneda
9,005,255 B2 * 4/2015 Lewis ................ A61B 17/8061 606/291
9,408,647 B2 * 8/2016 Cheney .............. A61B 17/8872
11,426,185 B2 8/2022 Zakhary et al.

OTHER PUBLICATIONS

Wright Medical Technology, Inc., "Mini Maxlock Extreme, ISO Plate", Surgical Technique, Apr. 13, 2016.

* cited by examiner

*Primary Examiner* — Andrew Yang
(74) *Attorney, Agent, or Firm* — DUANE MORRIS LLP

(57) ABSTRACT

A system includes an intraosseous sliding osteotomy (ISO) plate including a body extending between a first end, a second end, a first surface, a second surface, and a perimeter wall. The body defines at least one fastener aperture extending from the first surface to the second surface. A plate handle is configured to be coupled to the ISO plate. The plate handle includes a body including a handle portion and a head portion. The head portion defines at least one aperture. A locking element includes a locking portion sized and configured to extend through the at least one aperture defined in the head portion of the plate handle to couple the plate handle to the ISO plate.

25 Claims, 24 Drawing Sheets

INTRAOSSEOUS SLIDING OSTEOTOMY SYSTEM AND METHOD

CROSS-REFERENCE TO RELATED APPLICATIONS

This application is a continuation of U.S. patent application Ser. No. 17/814,889, filed on Jul. 26, 2022, which is a continuation of U.S. patent application Ser. No. 16/546,628, filed on Aug. 21, 2019 (now U.S. Pat. No. 11,426,185), which claims benefit of U.S. Provisional Application Ser. No. 62/774,373, filed on Dec. 3, 2018, entitled "INTRAOSSEOUS SLIDING OSTEOTOMY SYSTEM AND METHOD," the entire contents of which are incorporated herein by reference.

BACKGROUND

The forefoot includes five toes (which are also known as "phalanges") and connecting long bones (or "metatarsals"). Several small bones together comprise a phalanx or toe. The phalanges are connected to the metatarsals at the ball of the foot. The forefoot balances pressure on the ball of the foot and bears a substantial amount of the body weight. The forefoot is often the subject of trauma, such as results from falls, vehicle, crashes and dropped objects. These accidents often result in severe fractures and/or dislocations. In addition, there are several conditions which result from congenital deformation or which arise as a result of repeated use type injuries. Surgical intervention that includes surgical sectioning of bone or an "osteotomy" is often used to restructure the bones as a treatment for such conditions.

SUMMARY

In various embodiments, a system is disclosed. The system includes an intraosseous sliding osteotomy (ISO) plate including a body extending between a first end, a second end, a first surface, a second surface, and a perimeter wall. The body defines at least one fastener aperture extending from the first surface to the second surface. A plate handle is configured to be coupled to the ISO plate. The plate handle includes a body including a handle portion and a head portion. The head portion defines at least one aperture. A locking element includes a locking portion sized and configured to extend through the at least one aperture defined in the head portion of the plate handle to couple the plate handle to the ISO plate.

In various embodiments, a kit is disclosed. The kit includes an intraosseous sliding osteotomy (ISO) plate having a body extending between a first end, a second end, a first surface, a second surface, and a perimeter wall. The body defines at least one fastener aperture extending from the first surface to the second surface. The kit further includes a plate handle, a locking element configured to couple the ISO plate to the plate handle, a non-locking drill guide comprising a body and an insert receiving portion coupled to the body, and a broach comprising a broach handle and a broach insert.

In various embodiments, a method of forming an osteotomy is disclosed. The method includes a step of inserting a portion of a broach into a cut formed in a bone. The broach is rotated to displace a first portion of the bone from a second portion of the bone. An intraosseous sliding osteotomy (ISO) plate is inserted into the second portion of the bone. The ISO plate is coupled to a plate handle by a locking drill guide and the plate handle applies a force to the ISO plate. A first channel is formed in the first portion of the bone using a non-locking drill guide inserted at least partially into a first aperture defined in the ISO plate and a first fastener is inserted through the first aperture defined in the ISO plate into the first channel in the first portion of the bone to couple the ISO plate to the first portion of the bone.

BRIEF DESCRIPTION OF THE DRAWINGS

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

Figure 1A:
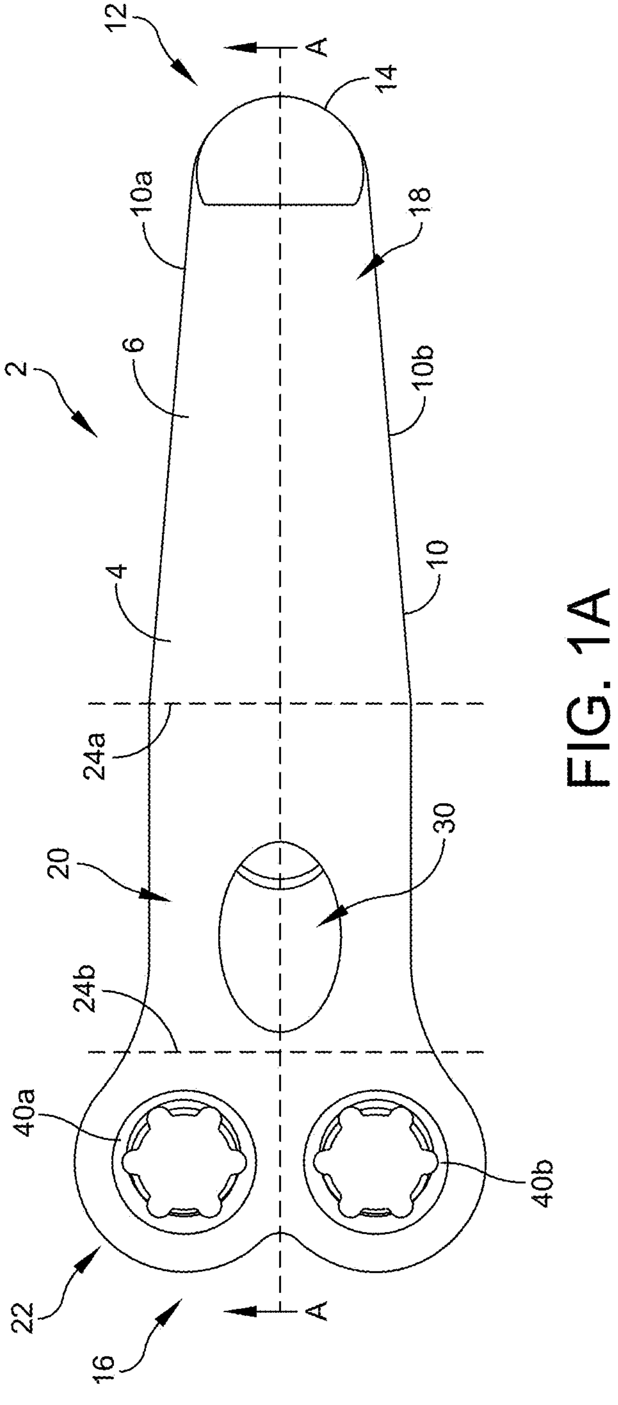
FIG. 1A illustrates an intraosseous sliding osteotomy (ISO) plate, in accordance with some embodiments.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top," "bottom," "proximal," "distal," "superior," "inferior," "medial," and "lateral" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected," refer to a relationship wherein structures are secured or attached to one another either directly or indirectly through intervening structures, as well as both movable or rigid attachments or relationships, unless expressly described otherwise. Like elements have been given like numerical designations to facilitate an understanding of the present subject matter.

As used herein, the term "substantially" denotes elements having a recited relationship (e.g., parallel, perpendicular, aligned, etc.) within acceptable manufacturing tolerances. For example, as used herein, the term "substantially parallel" is used to denote elements that are parallel or that vary from a parallel arrangement within an acceptable margin of error, such as +/−5°, although it will be recognized that greater and/or lesser deviations can exist based on manufacturing processes and/or other manufacturing requirements.

In various embodiments, systems and methods of forming an osteotomy in a first bone are disclosed. The system includes an intraosseous sliding osteotomy (ISO) plate. The ISO plate is configured to be inserted into a medullary canal of a first bone portion. The ISO plate includes one or more locking screw holes each configured to receive a locking screw therein and a compression screw hole configured to receive a compression screw therein. The system further includes a broach, a locking drill guide, a non-locking drill guide, a driver handle, driver insert, and a plurality of screws. In some embodiments, one or more elements of the system include an injected molded material.

Figure 1B:
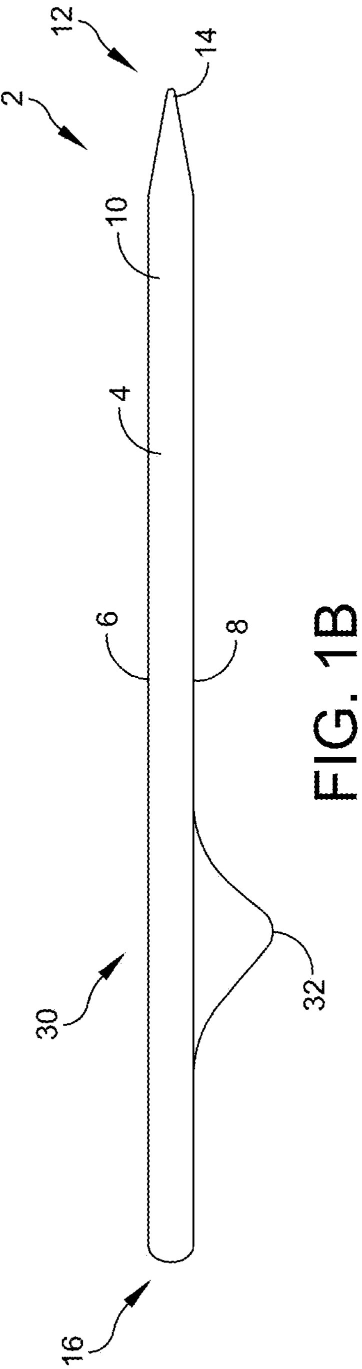
FIG. 1B illustrates a side view of the ISO plate of FIG. 1A, in accordance with some embodiments.
Figure 1C:
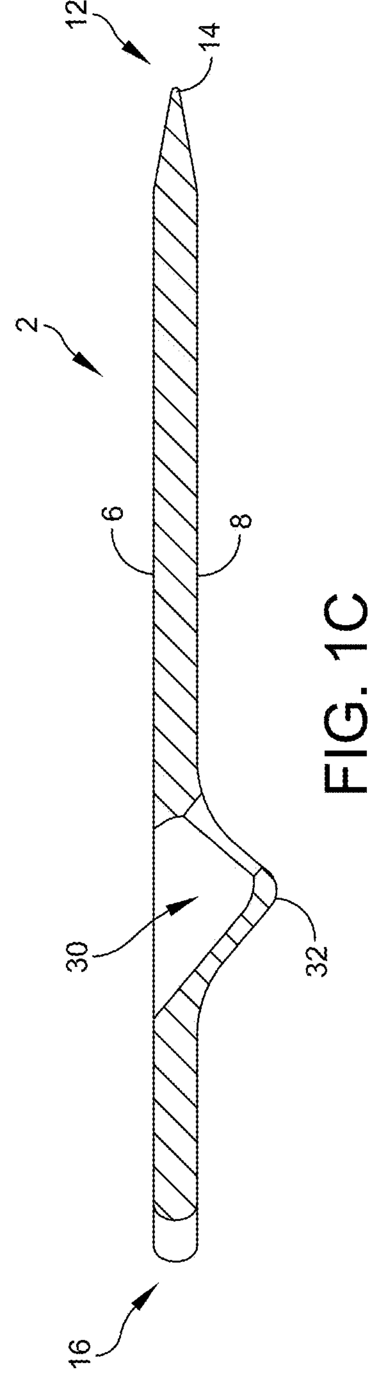
FIG. 1C illustrates a cross-section of the ISO plate of FIG. 1A taken along line A-A, in accordance with some embodiments.

In various embodiments, a method for inserting an ISO plate is disclosed. The method includes FIGS. 1A-1C illustrate an ISO plate 2, in accordance with some embodiments. The ISO plate 2 includes a body 4 extending between a first surface 6 and a second surface 8 and defined by a perimeter wall 10. In the illustrated embodiment, the first surface 6 and the second surface 8 define substantially parallel planes defining a substantially constant thickness, although it will be appreciated that the first surface 6 and the second surface 8 can be angled such that a thickness of the plate increases and/or decreases from a first end 12 to a second end 16.

In some embodiments, the plate 2 includes a plurality of portions defined by the perimeter wall 10. For example, as shown in FIG. 1A, the plate 2 can include a first (or insertion) portion 18 extending from a first end 12 of the plate 2 to a first mid-point 24*a* of the plate 2, a second (or compression) portion 20 extending from the first mid-point 24*a* to a second mid-point 24*b*, and a third (or fixation) portion 22 extending from the second mid-point to the second end 16 of the plate 2. Although mid-points 24*a*, 24*b* are provided for illustration purposes, it will be appreciated that the ISO plate 2 is continuous and that the mid-points 24*a*, 24*b* can be located at any suitable location on the plate 2 to denote continuous and/or separate portions 18-22. In some embodiments, one or more of the plate portions 18-22 can be omitted and/or combined.

In some embodiments, the insertion portion 18 defines a portion of the plate 2 sized and configured for insertion into a medullary canal of the bone. The insertion portion 18 defines a tapered portion having a thickness extending between the perimeter wall 10 that increases from the first end 12 to the first mid-point 24*a*. The perimeter wall 10 can define any suitable taper angle from the first end 12 to the first mid-point 24*a*. For example, in various embodiments, the perimeter wall 10 can include a first portion 10*a* and a second portion 10*b* defining the tapered insertion portion 18. The first portion 10*a* and/or the second portion 10*b* can define a taper angle with respect to a longitudinal axis 15, such as, for example, 5-15° (e.g., 5°, 7°, 8°, 9°, 10°, 11°, 13°, 15°, etc.), 5-25°, 5-75°, and/or any suitable angle. In some embodiments, the first portion 10*a* and the second portion 10*b* are parallel (define a 0° angle) and the insertion portion 18 defines a constant thickness.

In some embodiments, the insertion portion 18 includes a leading edge 14. The leading edge 14 can include a sloped or tapered edge configured to assist insertion of the plate 2 into the medullary canal, for example, by providing a smaller initial insertion area. The leading edge 14 can define a tapered portion extending from the first end 12 of the plate 2 and defining an increasing thickness. The thickness of the leading edge increases from a first thickness at the first end 12 to a second thickness equal to the thickness of the second portion 20 of the plate 2. In some embodiments, the leading edge 14 is sharpened to define a cutting edge. The leading edge 14 can define any suitable taper angle between the first surface 6 and the second surface 8, such as, for example, 5-15° (e.g., 5°, 7°, 8°, 9°, 10°, 11°, 13°, 15°, etc.), 5-25°, 5-75°, and/or any suitable angle. In some embodiments, the leading edge 14 is omitted and the insertion portion 18 defines a constant thickness equal to a plate thickness of the plate 2 at the second portion 20. The insertion portion 18 is configured to be inserted into a medullary canal of a first portion of a bone having an osteotomy formed therein, such as a first portion of a metatarsal.

In some embodiments, the compression portion 20 defines a non-locking fastener aperture 30 extending through the plate 2 from the first surface 6 to the second surface 8 at a predetermined angle. The predetermined angle can include any suitable angle with respect to the first surface 6 and/or the second surface 8. For example, in various embodiments, the non-locking fastener hole 30 can extend through the plate 2 at an angle between 35-45° (e.g., 35°, 37°, 39°, 40°, 41°, 43°, 45°, etc.), 30-50°, 5-90°, and/or any suitable angle. In some embodiments, the non-locking fastener aperture 30 is configured to direct a fastener inserted therethrough into the first portion of a bone having an osteotomy formed therein, such as the first portion of the metatarsal that previously received the insertion portion 18 therein.

In some embodiments, a shroud 32 extends from the second surface 8 of the plate 2. The shroud 32 defines a portion of the non-locking fastener hole 30 extending through the plate 2. The shroud 32 is configured to receive a head of a non-locking screw such that when a non-locking screw is inserted through the non-locking fastener hole 30, the non-locking screw head is contained entirely within the shroud 32. The shroud 32 can extend any suitable distance from the second surface 8 of the plate 2 sufficient to allow the head of the non-locking screw to be positioned entirely within the shroud 32.

In some embodiments, the plate 2 includes a plurality of locking fastener apertures 40*a*, 40*b* extending from the first surface 6 to the second surface 8 of the plate 2. The locking fastener apertures 40*a*, 40*b* can include apertures configured to receive a locking fastener (e.g., an "Ortholoc® 3Di™" locking screw sold by Wright Medical Technology, Inc. of Memphis, TN), inserted therethrough. The fastener may be disposed transversely or obliquely, relative to the fastener aperture 40*a*, 40*b*. In some embodiments, polyaxial screws can be inserted with an angle of 0.0 to about 15 degrees from the transverse axis of the locking fastener aperture 40. In some embodiments, polyaxial screws such as Ortholoc 3Di™ locking screws or non-locking screws sold by Wright Medical Technology, Inc. of Memphis, TN may be utilized. In some embodiments, the locking fastener apertures 40*a*, 40*b* are configured to direct a fastener inserted therethrough into a second portion of a bone having an osteotomy formed therein, such as a second portion of a metatarsal. U.S. Pat. No. 9,005,255 is incorporated herein by reference in its entirety.

Figures 2A, 2B:
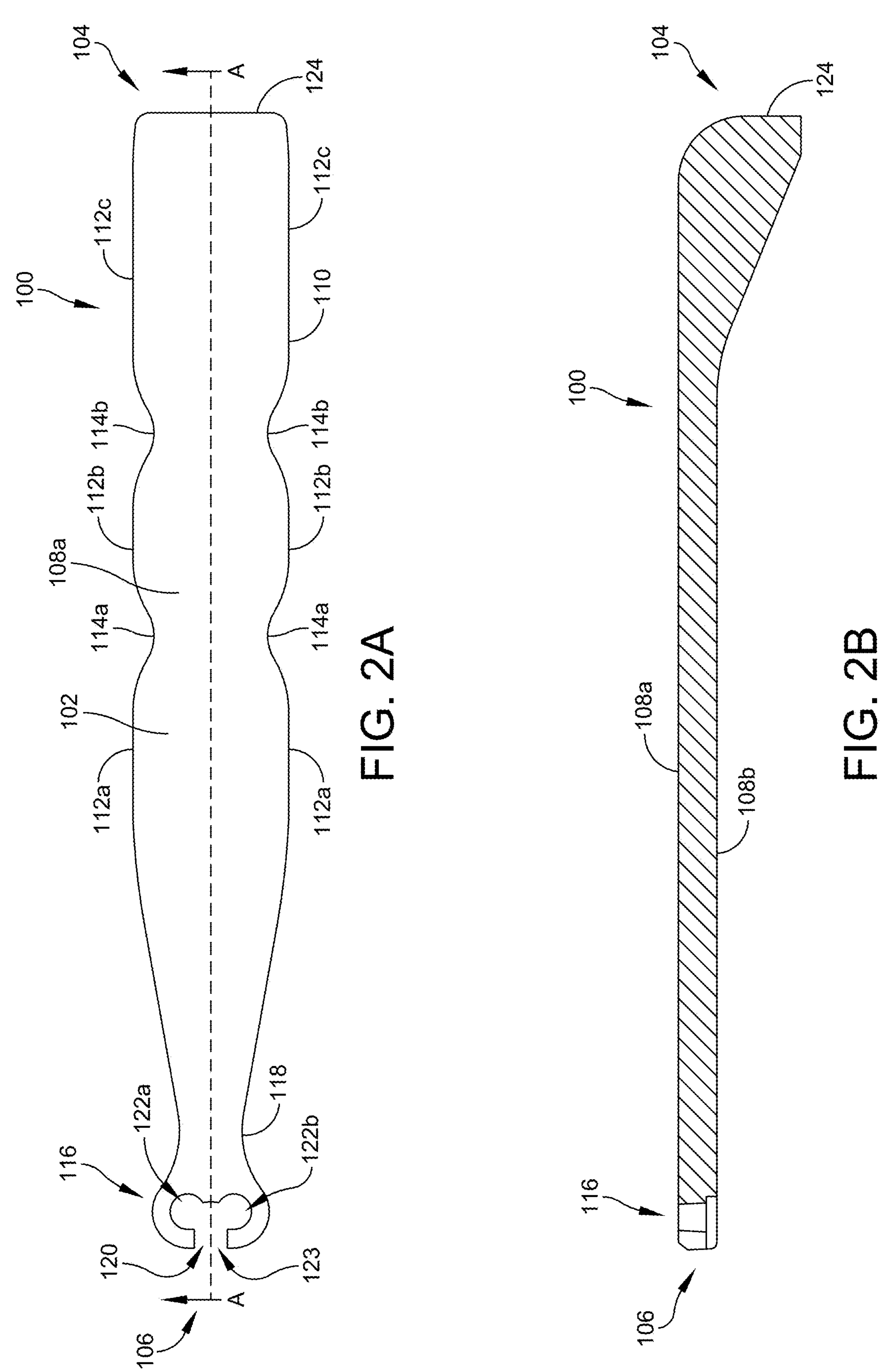
FIG. 2A illustrates a plate handle configured to be coupled to an ISO plate, in accordance with some embodiments.
FIG. 2B illustrates a cross-section of the plate handle of FIG. 2A taken along line A-A, in accordance with some embodiments.

FIGS. 2A-2B illustrate a plate handle 100 configured to be coupled to the ISO plate 2 of FIGS. 1A-1C, in accordance with some embodiments. The plate handle includes a body 102 extending from a first (or proximal) end 104 to a second (or distal) end 106. The body 102 is defined by an upper surface 108*a*, a lower surface 108*b*, and a perimeter 110. In some embodiments, the body 102 generally extends along a longitudinal axis 112 extending from the first end 104 to the second end 106. The perimeter 110 defines a profile sized and configured to be gripped by a user, such as a surgeon. For example, in various embodiments, the perimeter 110 defines a plurality of peaks 112*a*-112*c* and valleys 114*a*-114*b* on each side configured to facilitate gripping and/or manipulation by a user.

In some embodiments, the plate handle 100 includes a handle head 116 positioned at a distal end 106 of the body 102. The handle head 116 is coupled to the body 102 by a neck 118. The neck 118 defines a thickness less than the average thickness of the plate body 102. The handle head 116 defines an opening sized and configured to receive at least one locking drill guide (described in greater detail with respect to FIGS. 3A-3B) therein. For example, in the illustrated embodiment, the handle head 116 defines a generally reverse C-shaped body having an opening 120 defined by a first circular portion 122*a*, a second circular portion 122*b*, and a channel 123 extending from the circular portions 122*a*, 122*b* to a distal edge of the reverse C-shaped body. Although specific embodiments are illustrated, it will be appreciated that the handle head 116 can define any suitable shape having at least one opening configured to receive at least one locking drill guide therethrough, such as, for example, a generally "O" or "0" shaped opening, a generally "8" or "B" shaped opening, etc. The circular portions 122*a*, 122*b* can be continuous (as shown in the illustrated embodiment) or discontinuous (for example, in a "B" shaped embodiment) and can define an opening extending to an outer edge of the handle head 116 (for example, in a "C" shaped embodiment as illustrated) or can be closed (for example, in a "O" or "B" shaped embodiment.)

In some embodiments, the handle body 102 defines a tapered portion 126 adjacent a proximal end 104 of the body 102. The tapered portion 126 includes a portion of the body 102 having a thickness that increases from a first thickness to a second, greater thickness towards the proximal end 104 of the body 102. In some embodiments, the first thickness is the thickness of the remainder of the handle body 102. The tapered portion 126 functions as a stop or movement-limiting portion to maintain a user's hand position on the handle 100 during use. In some embodiments, a proximal edge 124 of the body 102 defines an impact or striking surface configured to receive an impact during insertion of a plate 2 coupled to the handle 100.

In some embodiments, the plate handle 100 (or a portion thereof) can be formed by injection molding material such as polycarbonate (PC), polyacrylamide (such as Ixef® PARA available from Solvay Group, Belgium), and/or any other suitable injection molding material. The injection molding can be formed over one or more structural features, such as ribs, lattice, etc. to provide increased strength and/or to withstand insertion forces applied to the plate handle 100 during insertion of an ISO plate 2. In some embodiments, the plate handle 100 (or a portion thereof) is formed of a metal material and can be formed using any suitable process, such as by stamping, bending, cutting, milling, etc.

Figure 3A:
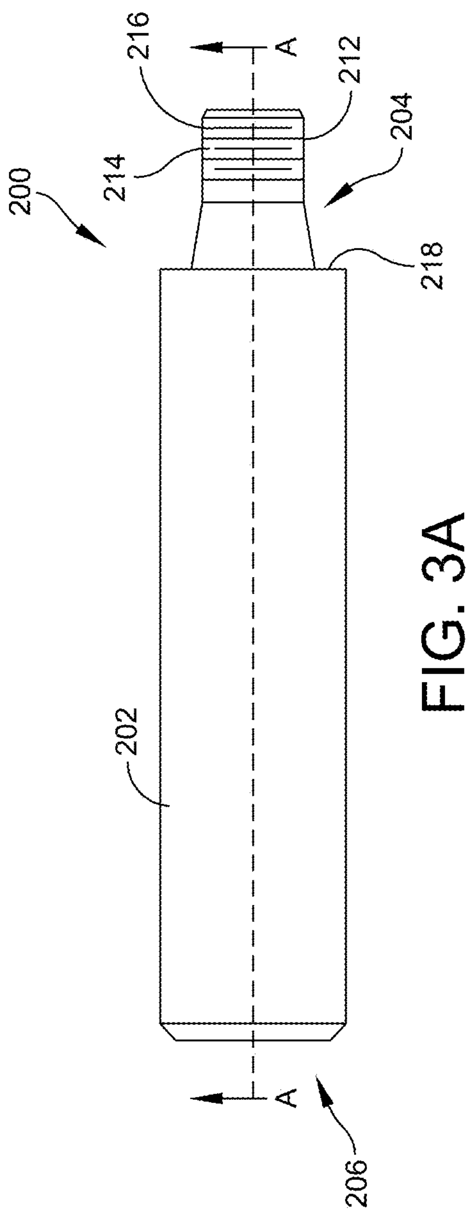
FIG. 3A illustrates a locking drill guide configured to be coupled to a plate handle, in accordance with some embodiments.
Figure 3B:
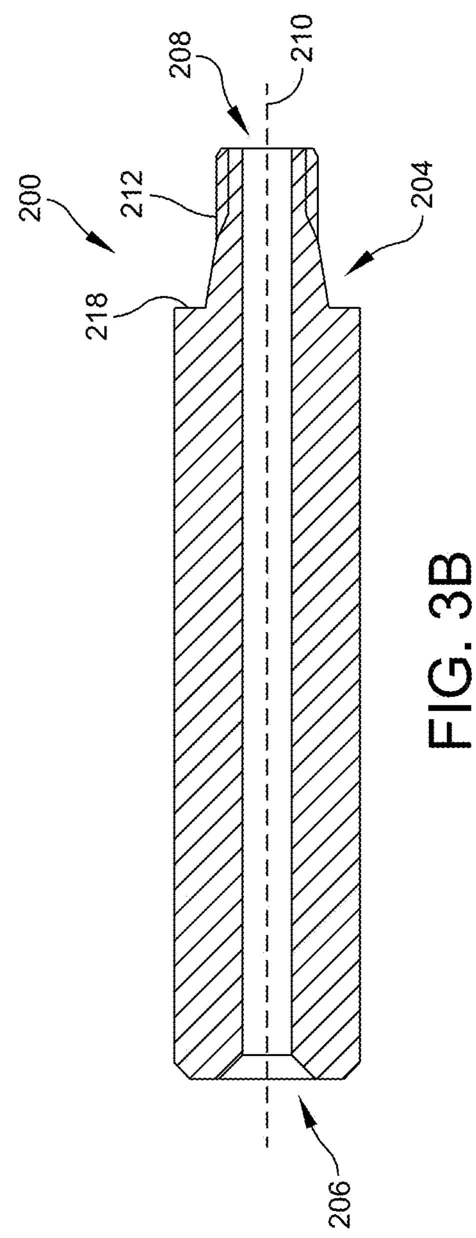
FIG. 3B illustrates a cross-section of the locking drill guide of FIG. 3A taken along line A-A, in accordance with some embodiments.

FIGS. 3A-3B illustrate a locking drill guide 200 configured to couple the plate 2 to the plate handle 100, in accordance with some embodiments. The locking drill guide 200 includes a body 202 extending from a first end 204 to a second end 206. In the illustrated embodiment, the body 202 includes a generally cylindrical body extending the first end 204 to the second end 206, although it will be appreciated that the body 202 can include any suitable shape, such as a regular and/or irregular geometric shape. The body 202 defines a channel 208 (shown in FIG. 3B) extending therethrough from the first end 204 to the second end 206. In the illustrated embodiment, the channel 208 extends parallel to a longitudinal axis 210 of the body 202, although it will be appreciated that the channel 208 can extend through the body 202 at any suitable angle with respect to the longitudinal axis 210 of the body.

A locking extension 212 extends from a first end 204 of the body 202. The locking extension 212 is formed integrally with the body 202 and defines a portion of the channel 208 therethrough. The locking extension 212 includes at least one locking feature 214 configured to couple the locking drill guide 200 to an ISO plate, such as the ISO plate 2 discussed in conjunction with FIGS. 1A-1C. In the illustrated embodiment, the locking feature 214 includes a thread 216 sized and configured to couple to a thread included in at least one locking aperture defined in the ISO plate 2, although it will be appreciated that other suitable locking features, such as pins, fins, press-fit features, etc. can be used to couple the locking drill guide 200 to the ISO plate 2.

The first end 204 of the body 202 defines a handle contact edge 218 sized and configured to contact a portion of a head 116 of plate handle 100. For example, in the illustrated embodiments, the head 116 defines a first circular opening 122*a* and a second circular opening 122*b* each sized and configured to receive the locking extension 212 therethrough. When the locking extension 212 is inserted through one of the first or second circular openings 122*a*, 122*b*, the contact edge 218 contacts a surface of the head 116. When the locking extension 212 is locked to the plate 2, for example by rotating the locking drill guide 200 to engage the threads 216 with a locking fastener aperture 40*a*, the handle head 116 is compressed between the plate 2 and the contact edge 218 to couple the plate 2, the handle 100, and the locking drill guide 200 in a press-fit engagement. The assembly of the plate 2, handle 100, and locking drill guide 200 can be manipulated using the handle 100 to insert the plate 2 at least partially into a medullary canal of a bone.

In some embodiments, the channel 208 defines a predetermined interior shape configured to couple to and/or interface with a driver inserted into the channel 208. For example, in various embodiments, the channel 208 can define an interior perimeter such as a hexagon or star shape configured to interface with a driver to rotate the locking drill guide 200 to couple the locking drill guide 200 to the plate 2.

In some embodiments, the outer surface of the locking drill guide 200 includes one or more features configured to provide increased grip (e.g., friction) to a user when attaching and/or removing the locking drill guide 200 to the ISO plate 2 and/or the plate handle 100. For example, in various embodiments, the locking drill guide 200 can include grooves, knurling, etching, and/or any other suitable surface treatment. In some embodiments, the locking drill guide 200 includes a torx-feature (or other coupling feature) for fixing the plate 16 to the insertion handle 106 and/or separate the plate 16 from the insertion handle 106.

In some embodiments, the locking drill guide 200 (or a portion thereof) can be formed by injection molding material such as polycarbonate (PC), polyacrylamide, and/or any other suitable injection molding material. The injection molding can be formed over one or more structural features, such as ribs, lattice, etc. to provide increased strength and/or to withstand forces applied during attachment and/or removal of the locking drill guide 200. In some embodiments, the locking drill guide 200 (or a portion thereof) is formed of a metal material formed by any suitable process, such as by stamping, bending, drilling, milling etc.

Figures 4A, 4B:
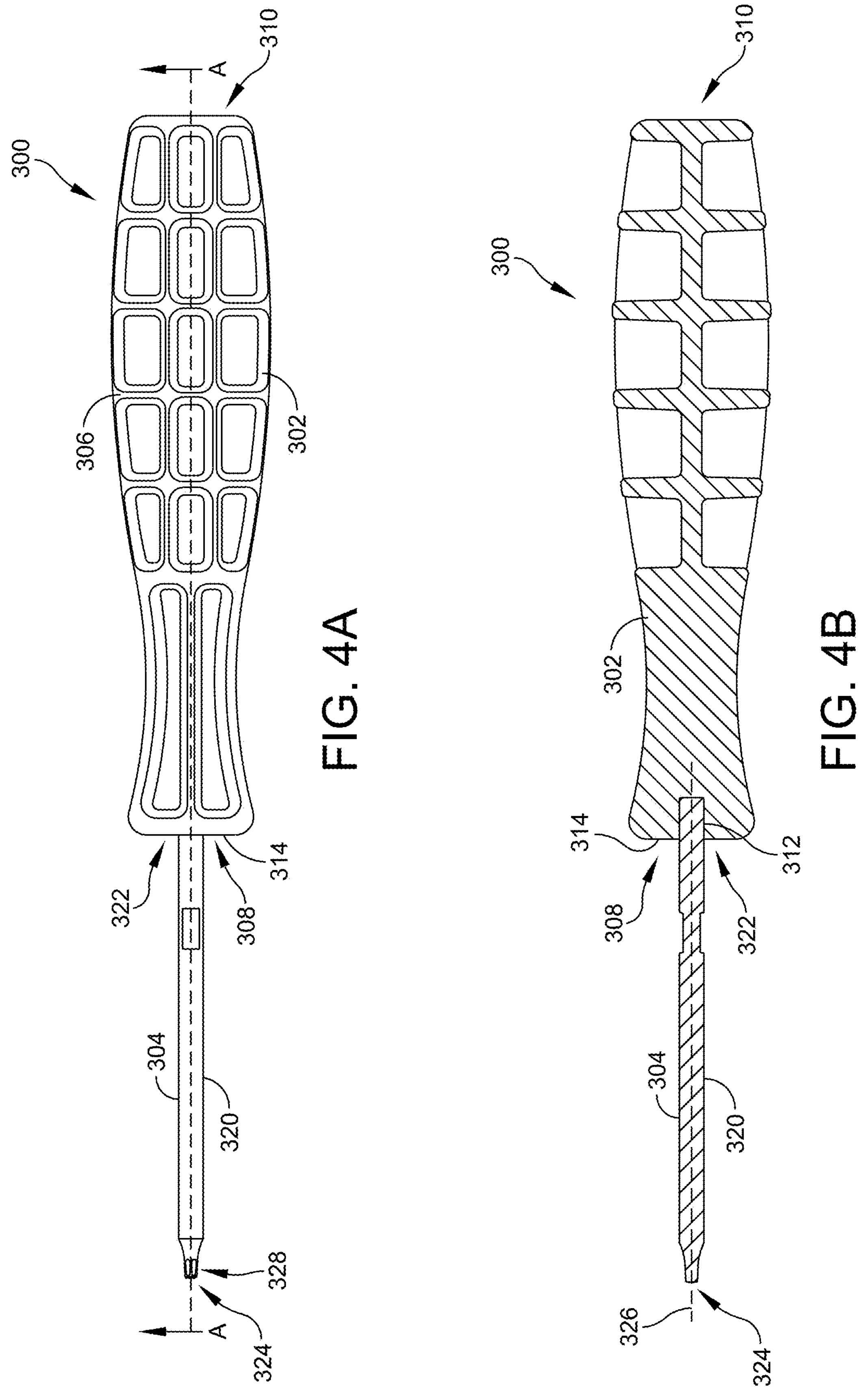
FIG. 4A illustrates a driver configured to be coupled to one or more elements of an ISO plate system, in accordance with some embodiments.
FIG. 4B illustrates a cross-section of the driver of FIG. 4A taken along line A-A, in accordance with some embodiments.

FIGS. 4A-4B illustrate a driver 300 including a driver handle 302 and a driver insert 304 configured to be engage and rotate at least one element of a plate inserter system, such as the locking drill guide 200 described in conjunction with FIGS. 3A-3B. The driver handle 302 includes a body 306 extending between a first end 308 and a second end 310. The driver handle 302 defines a channel 312 extending from a distal face 314 of the driver handle into the body 306. The driver handle 302 is similar to a screwdriver or other tool handle and is configured to be gripped by a user.

The channel 312 is sized and configured to receive a portion of a driver insert 304 therein. The driver insert 304 includes a body 320 extending from a first end 322 to a second end 324 substantially along a longitudinal axis 326. The first (or proximal) end 322 of the driver insert 304 is configured to be inserted into and retained within the channel 312 defined by the driver handle 302. The driver insert 304 can be permanently or releasably coupled to the driver handle 302. For example, in some embodiments, the driver handle 302 is overmolded onto the driver insert 304 to permanently retain the driver insert 304 within the channel 312.

The second (or distal) end 324 of the driver insert 304 defines a driver head 328. The driver head 328 has a complimentary shape with respect to the interior perimeter of a channel 208 defined in the locking drill guide 200. The driver head 328 is configured to interface with and couple to the fastener configured to be inserted through the ISO plate 2, such as a locking fastener and/or a non-locking fastener. For example, in embodiments, the driver head 328 defines a complimentary hexagon shape configured to fit within and interface with a hexagonal channel formed in a first end of a locking and/or non-locking fastener. It will be appreciated that any suitable shape can be defined by the head of the fastener and the driver head 328.

In some embodiments, the driver 300 (or a portion thereof) can be formed by injection molding material such as polycarbonate (PC), polyacrylamide, and/or any other suitable injection molding material. For example, in some embodiments, the driver handle 302 is formed of an injection molding material by overmolding the driver handle 302 over a driver insert 304. The injection molding can be formed over one or more structural features, such as ribs, lattice, etc. to provide increased strength and/or to withstand forces applied during insertion of one or more fasteners using the driver 300. In some embodiments, the driver 300 (or a portion thereof) is formed of a metal material formed by any suitable process, such as by stamping, bending, drilling, milling etc. For example, in some embodiments, the driver insert 304 is formed of a metal material.

FIGS. 5A-5E illustrate a drill guide 400 configured to guide formation of a channel in a bone, in accordance with some embodiments. The drill guide 400 includes a handle portion 402 and a head portion 404. The handle portion 402 extends from a first end 406*a* to a second end 406*b* substantially along a central longitudinal axis 407 and is defined by an upper surface 408*a*, a lower surface 408*b*, and a perimeter wall 410. The handle portion 402 has a thickness extending between the upper surface 408*a* and the lower surface 408*b*. In some embodiments, the handle body 406 defines a plurality of gripping features 410 configured to add friction and/or otherwise assist a user in gripping the handle 402.

A head portion 404 is coupled to a distal end 406*b* of the handle portion 402. The head portion 404 includes a neck 412 extending from the handle portion 402 and an insert receiving portion 414. The neck 412 can include a first portion 416*a* and a second portion 416*b* coupled by an offset portion 418. The offset portion 418 positions the second portion 416*b* within a plane that is vertically offset from a plane of the first portion 416*a*. In the illustrated embodiments, the first portion 416*a* and the second portion 416*b* are substantially parallel, although it will be appreciated that the first portion 416*a* and the second portion 416*b* can define an offset angle therebetween. The offset portion 418 extends a predetermined distance to position the second portion 416*b* and the insert receiving portion 414 at a predetermined vertical offset from the handle portion 402. In some embodiments, the neck 412 can include an offset angle with respect to the handle such that the insert receiving portion 414 is positioned at a horizontal offset with respect to the handle portion 414.

The insert receiving portion 414 includes a body 420 defining an insert channel 422 extending from a first end 424*a* of the body to a second end 424*b* of the body. The insert channel 422 is configured to receive a drill guide insert therein. In the illustrated embodiment, the body 420 defines a hollow cylinder, although it will be appreciated that the body 420 can include any suitable shape defining an insert channel 422 therethrough. Furthermore, the channel 422 can include any suitable shape complimentary to an outer surface of a drill guide insert 430, as described in greater detail below. In the illustrated embodiment, the insert channel 422 defines a central longitudinal axis 426 extending substantially orthogonal to the central longitudinal axis 407 of the handle portion 402, although it will be appreciated that the central longitudinal axis 426 of the insert channel 422 can be offset at a predetermined angle with respect to the central longitudinal axis 407 of the handle portion 402.

Figure 5A:
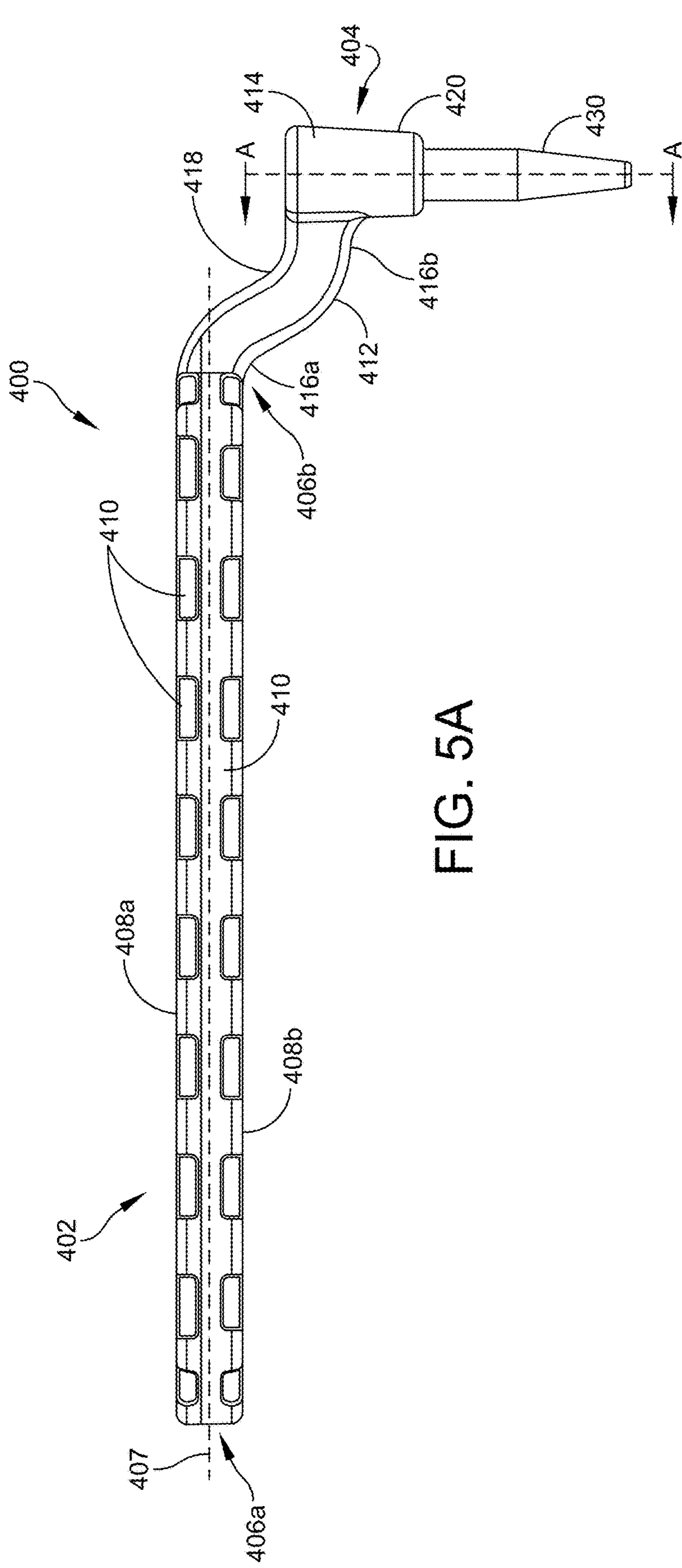
FIG. 5A illustrates a drill guide configured to be coupled to an ISO plate, in accordance with some embodiments.
Figure 5B:
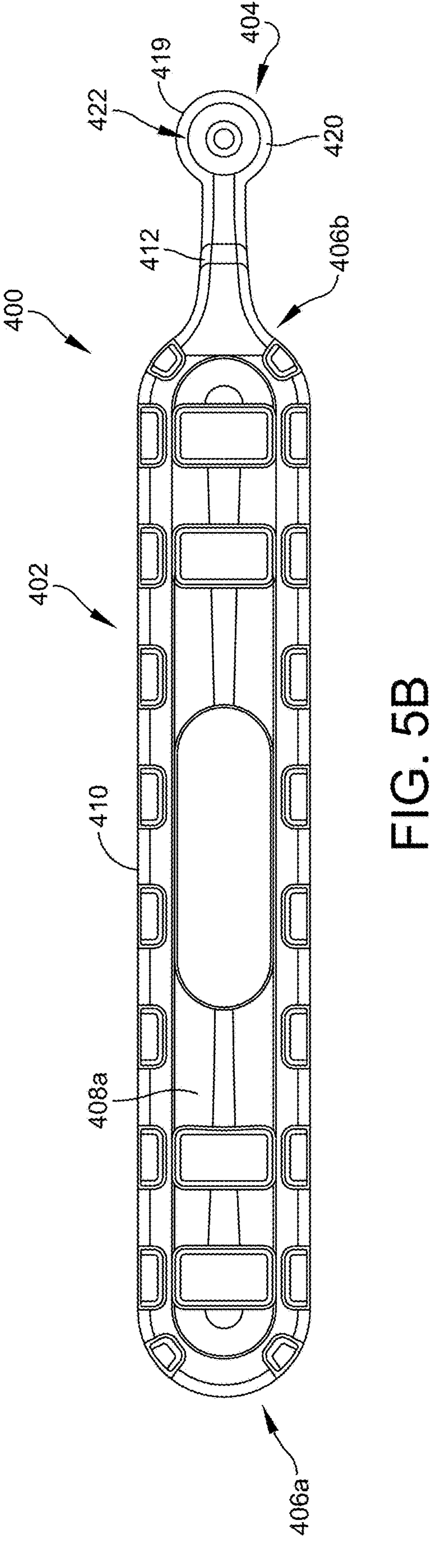
FIG. 5B illustrates a top view of the drill guide of FIG. 5A, in accordance with some embodiments.
Figure 5D:
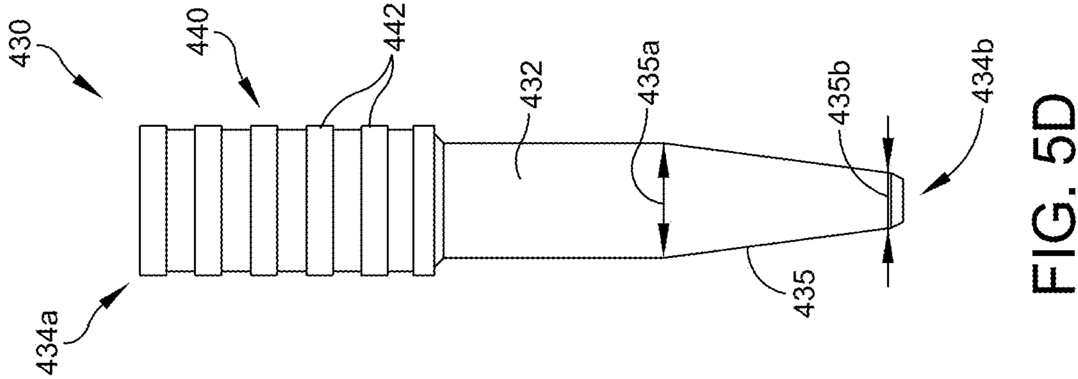
FIG. 5D illustrates a drill guide insert configured to be coupled to the drill guide of FIG. 5A, in accordance with some embodiments.
Figure 5C:
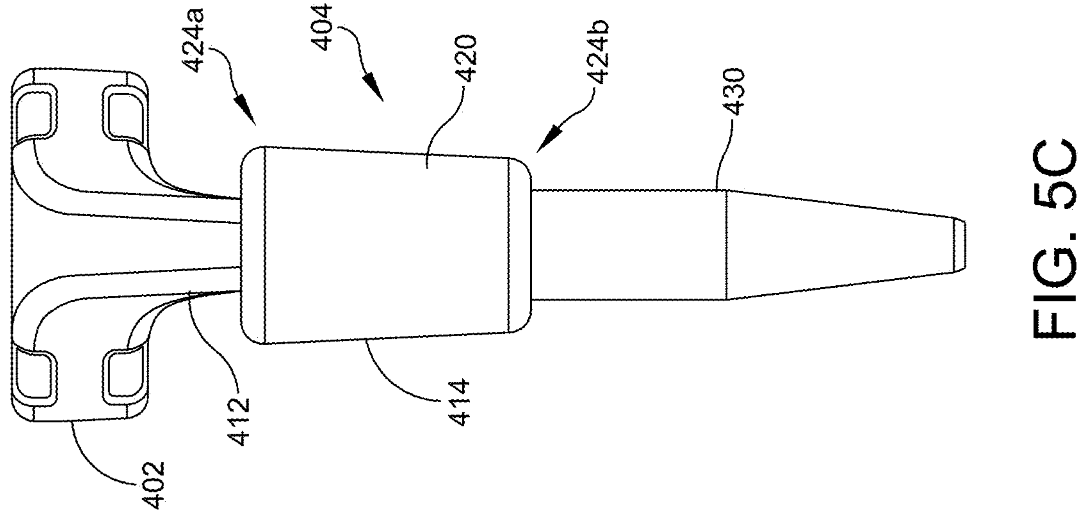
FIG. 5C illustrates a front view of the drill guide of FIG. 5A, in accordance with some embodiments.
Figure 5E:
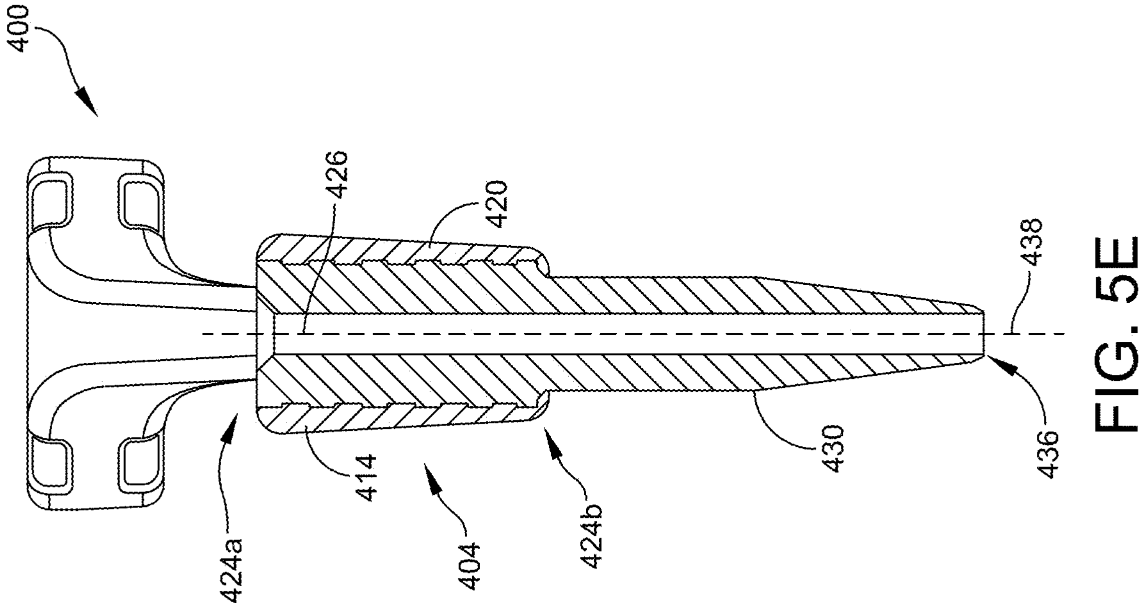
FIG. 5E illustrates a cross-section of an insert guide portion and an drill guide insert along line A-A of FIG. 5C, in accordance with some embodiments.

The drill guide insert 430 (as illustrated in FIG. 5D) includes a substantially cylindrical body 432 extending from a first end 434*a* to a second end 434*b*. In some embodiments, the body 432 has defines an insertion portion 435 that has an outer diameter that tapers (or expands) from a first diameter 435*a* to a second diameter 435*b* at a second end 434*b*. The cylindrical body 432 defines a guide channel 436 extending from a first end 434*a* to a second 434*b*. In the illustrated embodiment, the guide channel 436 extends substantially along and parallel to a central longitudinal axis 438 of the cylindrical body 432, although it will be appreciated that the guide channel 436 can extend through the body 432 at an angle to and/or offset from the central longitudinal axis 438.

The guide channel 436 includes a circumference sized and configured to receive a drill bit therethrough. The guide channel 436 is configured to guide the drill bit for drilling into a portion of a bone, such as a metatarsal. In some embodiments, the guide channel 436 defines a circumference substantially equal to a circumference of a drill bit configured to be inserted therein such that the drill bit is able to rotate about a horizontal axis and move vertically but is prevented from moving laterally and/or rotate about any other axis.

In some embodiments, the drill guide insert 430 includes a retaining portion 440 including one or more retention features 442 configured to maintain the drill guide insert 430 within the channel 422 defined by the insert receiving portion 414 of the drill guide 400. For example, in the illustrated embodiment, the retention features 442 include a plurality of ribs having an increased diameter (or circumference) with respect to the body 432 of the drill guide insert 430. The increased diameter of the ribs creates a friction fit against the inner surface of the channel 422 and maintains the drill guide insert 430 in a fixed position with respect to the insert receiving portion 414. Although embodiments are illustrated with ribs, it will be appreciated that any suitable retention feature, such as threads, ribs, pins, etc. can be alternatively and/or additionally included on the drill guide insert 430.

As shown in FIG. 5A, the drill guide insert 430 is sized and configured to be received within the insert channel 422 defined by the insert receiving portion 414. As noted above, in some embodiments, the body 432 of the drill guide insert 430 includes an outer diameter that tapers from a first diameter 435*a* to a second diameter 435*b*. The first diameter 435*a* is less than an inner diameter of the insert channel 422 such that the first end 434*a* of the drill guide insert 430 can pass into and freely through the insert channel 422. In some embodiments, the second diameter 435*b* is greater than the inner diameter of the insert channel 422 such that a portion of the drill guide 430 positioned adjacent the second end 434*b* is prevented from passing into and/or through the insert channel 422. In some embodiments, the taper of the body 432 of the drill guide insert 430 is selected to provide a friction fit with an inner surface of the guide channel 422, although it will be appreciated that the second end 434*b* of the drill guide insert 430 can include a lip configured to abut the insert receiving portion 414 without providing a friction fit within the guide channel 422.

In the illustrated embodiment, when the drill guide insert 430 is positioned within the guide channel 422, the central longitudinal axis 426 of the insert channel 422 and the central longitudinal axis 438 of the cylindrical body 432 are aligned. A user can manipulate the handle portion 402 to position a head portion 404 (and therefore the drill guide insert 430) in a desired position for formation of a hole within a bone. For example, in some embodiments, the drill guide insert 430 is sized and configured to be partially inserted into one of a locking aperture 40*a*, 40*b* and/or a non-locking aperture 30 of the ISO plate 2.

Figures 6A, 6B:
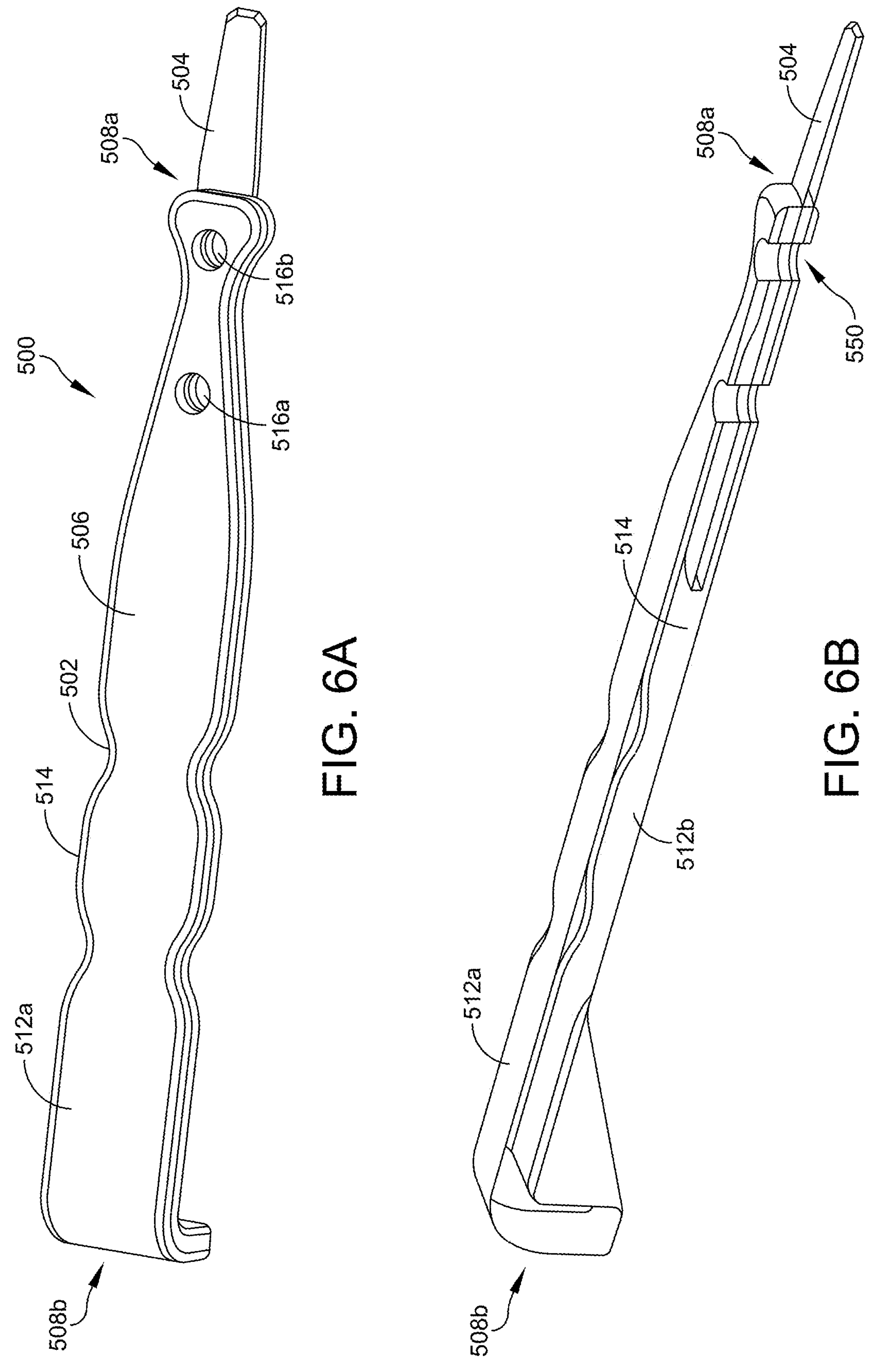
FIG. 6A illustrates a broach including a handle and an insert, in accordance with some embodiments.
FIG. 6B illustrates a cross-section of the broach of FIG. 6A, in accordance with some embodiments.
Figure 6C:
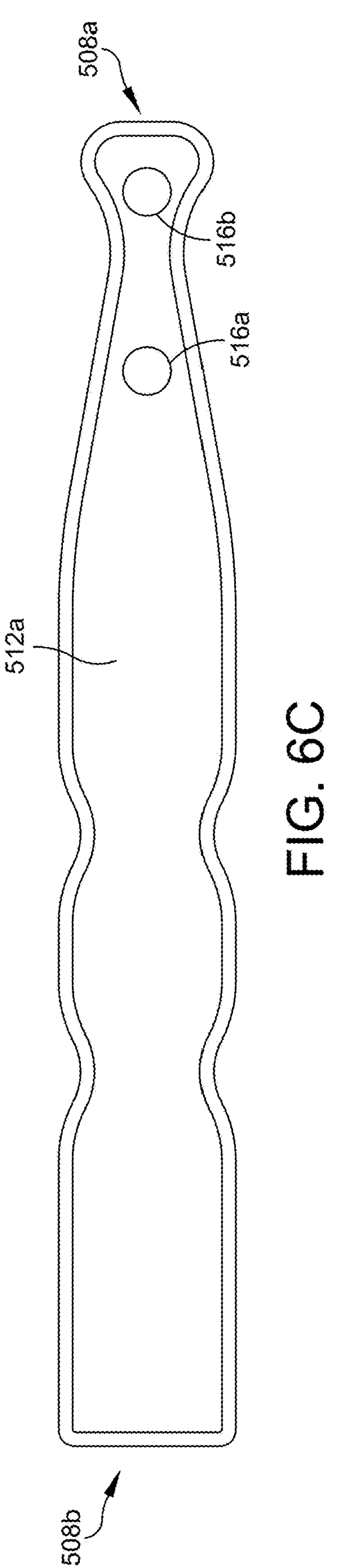
FIG. 6C illustrates the handle of the broach of FIG. 6A, in accordance with some embodiments.
Figure 6D:
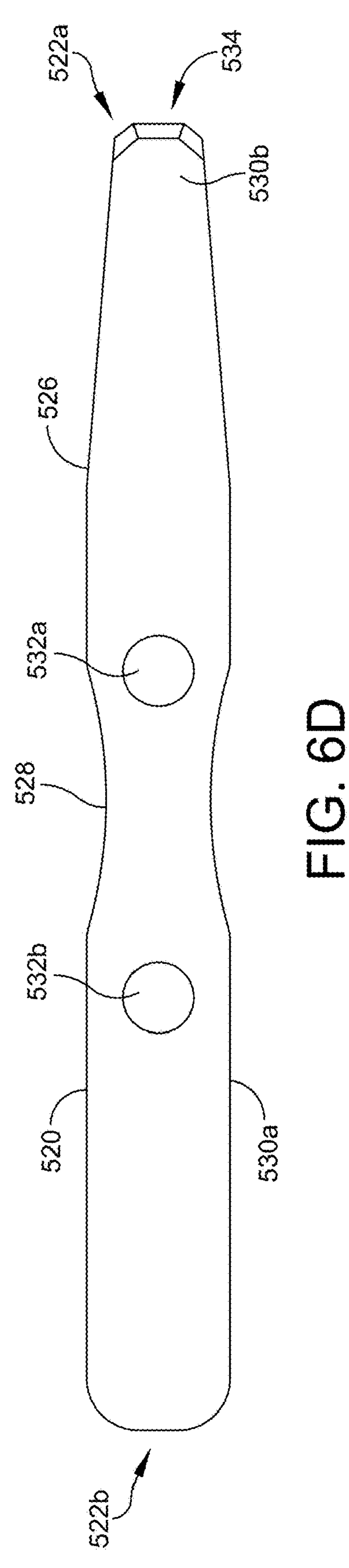
FIG. 6D illustrates the insert of the broach of FIG. 6A, in accordance with some embodiments.

FIGS. 6A-6C illustrate a broach 500 including a handle 502 and an insert 504, in accordance with some embodiments. The handle 502 includes a body 506 extending from a first end 508*a* to a second end 508*b* substantially along a central longitudinal axis 510 and defined by a first surface 512*a*, a second surface 512*b*, and a perimeter wall 514. The handle 502 defines a first fastener aperture 516*a* and a second fastener aperture 516*b* extending from the first surface 512*a* to the second surface 512*b*. In some embodiments, the first and second fastener apertures 516*a*, 516*b* are sized and configured to receive a fastener therein to couple the handle 502 to an insert 504, as described in greater detail below. In some embodiments, the handle 502 defines a slot or channel 550 extending from a first end 508*a* into the body 506 sized and configured to receive a portion of an insert 504 therein. In some embodiments, the channel is sized and configured to receive a portion of an insert 504 such that the first and second fastener apertures 516*a*, 516*b* are aligned with fastener apertures formed in the insert 504 (as described in greater detail below) when the insert 504 is inserted into the channel. In some embodiments, the insert 504 is overmolded by the first end 508*a* of the handle 502.

As illustrated in FIG. 6C, in some embodiments, an insert 504 includes a body 520 extending from a first end 522*a* to a second end 522*b* substantially along a central longitudinal axis 524 and defined by a first surface 526, a second surface (not shown), and a perimeter wall 528. The insert 504 includes a first portion 530*a* configured to be coupled to a handle 502 and a second portion 530*b* configured to be at least partially inserted into a cut formed in a bone, such as a metatarsal. The body 520 defines a plurality of fastener apertures 532*a*-532*c* extending from a first surface 526 to a second surface and sized and configured to receive a fastener therein. In some embodiments, one or more of the fastener apertures 532*a*-532*c* are positioned to align with fastener apertures 516*a*, 516*b* formed in the handle 502 when the insert 504 is positioned adjacent to and/or inserted into the handle 502.

As shown in FIG. 6A, the insert 504 is configured to be coupled to the handle 502 to define a broach 500 configured to assist in formation of an osteotomy in a bone, such as a metatarsal. As described in greater detail below, the second portion 530*b* of the insert 504 is configured to be inserted into a bone and leveraged to offset a first portion of a bone with a second portion of the bone to form an osteotomy. In some embodiments, a leading edge 534 of the insert 504 is configured to facilitate insertion into the bone. The leading edge 534 can be sharpened to define a cutting edge and/or include a thickness less than the thickness of the insert 504.

In some embodiments, the broach handle 502 (or a portion thereof) can be formed by injection molding material such as polycarbonate (PC), polyacrylamide, and/or any other suitable injection molding material. The injection molding can be formed over one or more structural features, such as ribs, lattice, etc. to provide increased strength and/or to withstand forces applied during insertion of the broach 500 and formation of an osteotomy in a bone. In some embodiments, the insert 504 (or a portion thereof) is formed of a metal material formed by any suitable process, such as by stamping, bending, drilling, milling etc.

Figure 7:
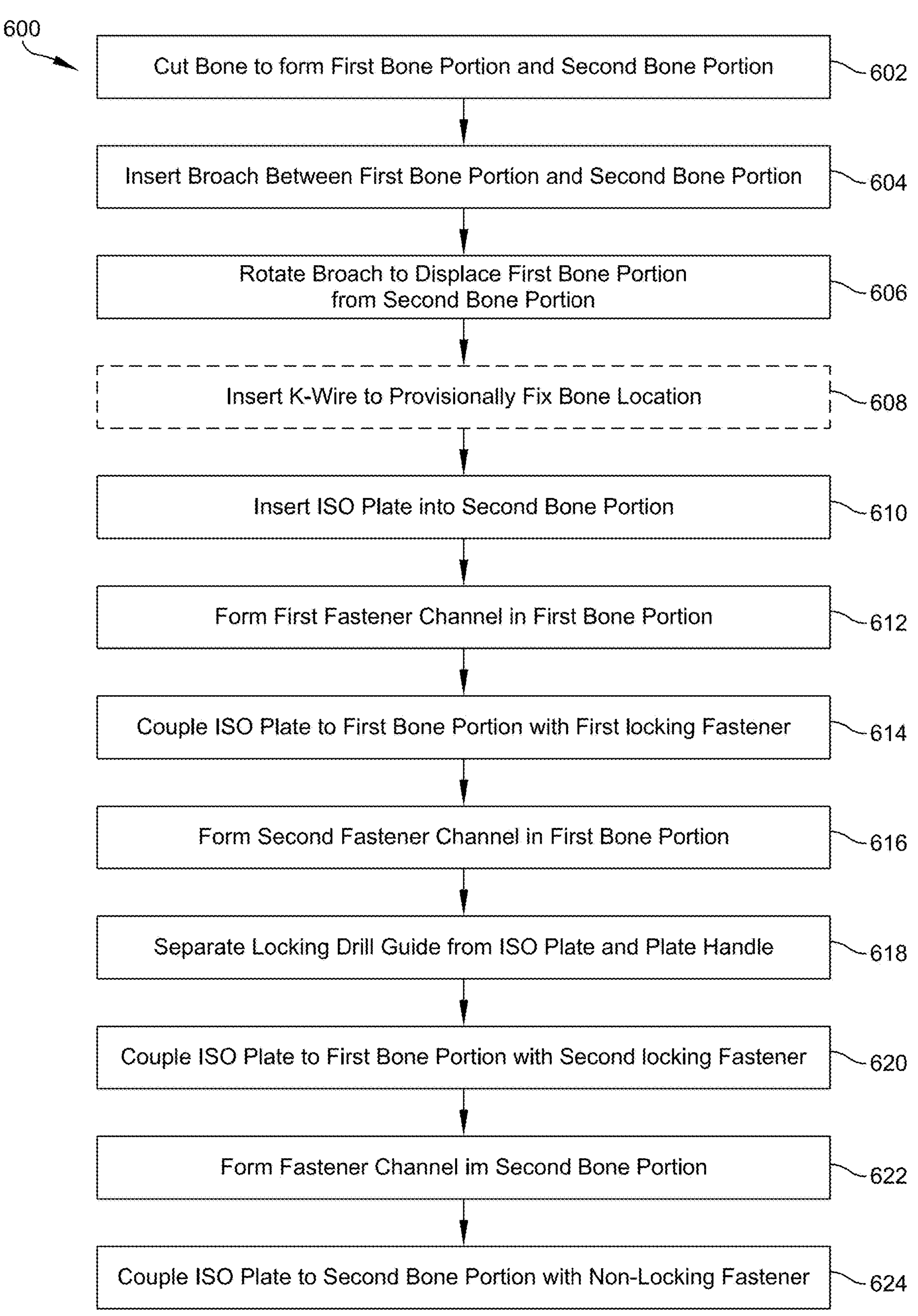
FIG. 7 illustrates a method of forming an osteotomy in a bone, in accordance with some embodiments.

FIG. 7 illustrates a method 600 of forming an osteotomy in a bone and FIGS. 8A-8I illustrate various steps of the method 600 performed at a surgical site 700, in accordance with some embodiments. At step 602, a cut 704 or osteotomy line is formed in a bone 702, such as a metatarsal. The cut 704 can be formed using any suitable instrument, such as a manual and/or electric cutting instrument such as a saw, burr, etc. The cut 704 extends through the bone 702 to generate a first bone portion 702*a* and a second bone portion 702*b*. For example, in some embodiments, the cut 704 is a distal transverse osteotomy formed through the first metatarsal at least 12 mm from an articular surface and just proximal to a capsular attachment, although it will be appreciated that the systems and methods disclosed herein can be used with any suitable bone using any appropriate surgical approach.

Figure 8A:
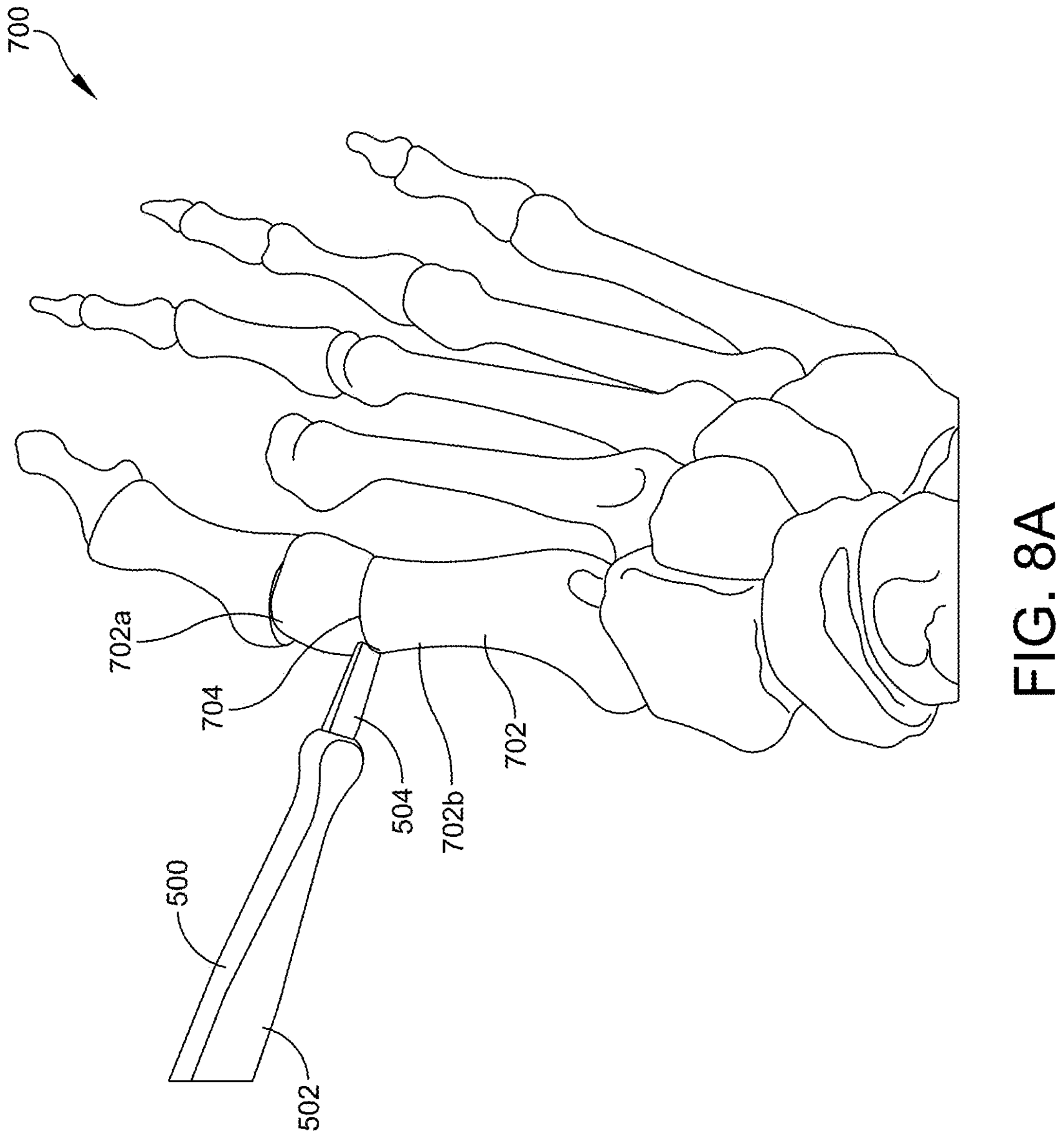
FIG. 8A illustrates a step of forming an osteotomy in a bone, in accordance with some embodiments.
Figure 8B:
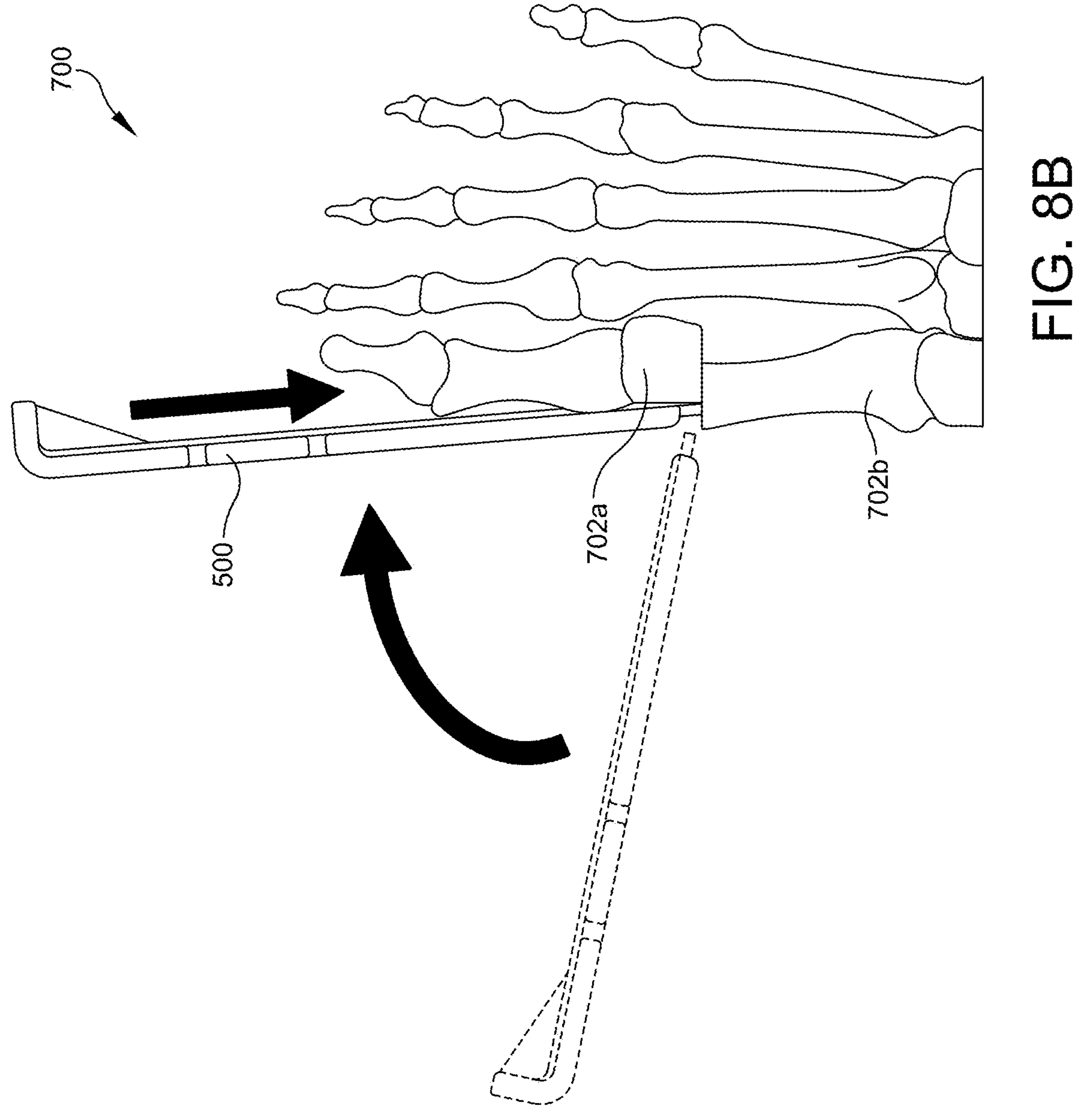
FIG. 8B illustrates a step of offsetting a first bone portion from a second bone portion using a broach, in accordance with some embodiments.

At step 604, and as illustrated in FIG. 8A, a broach 500 is partially inserted into the cut 704 between the first bone portion 702*a* and the second bone portion 702*b*. The broach 500 includes a handle 502 and an insert 540 as discussed above. The leading edge 534 of the insert 504 can be inserted into the cut 704 and a force applied to advance the insert 504. The force may be applied by a surgeon by pushing on the handle 402 and/or lightly striking the handle 502 with a striking instrument (e.g., hammer). At step 606, after inserting the broach 500, the broach is rotated (or leveraged) to displace the first bone portion 702*a* from the second bone portion 702*b*, as shown in FIG. 8B. In some embodiments, the broach handle is maintained parallel with a medial border of the foot during insertion. At optional step 608, a k-wire can be used to provisionally fix the bone location after shifting.

Figure 8C:
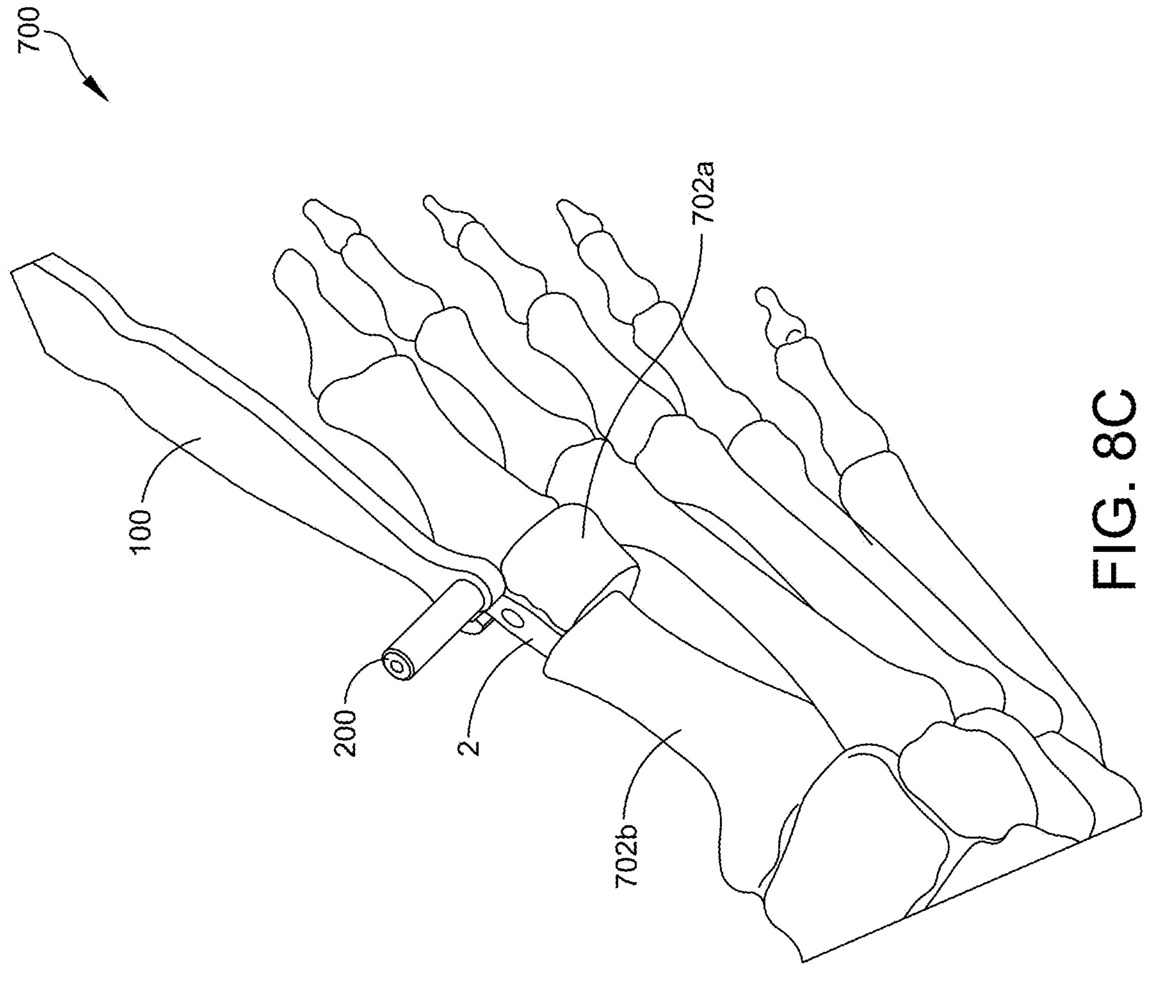
FIG. 8C illustrates a step of inserting an ISO plate into a second bone portion, in accordance with some embodiments.

At step 610, and as illustrated in FIG. 8C, an ISO plate, such as ISO plate 2 described above, is partially inserted into the second bone portion 702*b*. For example, in some embodiments, the ISO plate 2 is coupled to a plate handle 100 as illustrated in FIG. 2. The ISO plate 2 is coupled to the plate handle 100 by a locking drill guide 200. The locking drill guide 200 includes a locking extension 212 that extends through a portion of an opening 112 formed in the plate handle 100 and that is coupled to a locking aperture 40*b* formed in the ISO plate 2. The locking drill guide 200 locks the plate handle 100 and the ISO plate 2 in a fixed engagement and transfers a force applied to the plate handle 100 to the ISO plate 2.

The plate handle 100 is used to apply a force to the ISO plate 2. The leading edge 14 of the ISO plate 2 is sharpened to facilitate insertion into the interior of the second bone portion 702*b*. In some embodiments, a force is applied to the plate handle 100 by a striking instrument (e.g., hammer) to advance the ISO plate 2 into the second bone portion 702*b*. The ISO plate 2 is inserted to a predetermined depth within the second bone portion 702*b*. For example, in some embodiments, the ISO plate 2 is inserted into a cavity formed by the broach 400 until a portion of the plate handle 100 (such as the head 116) contacts the second bone portion 702*b* indicating the desired predetermined depth has been reached.

Figure 8D:
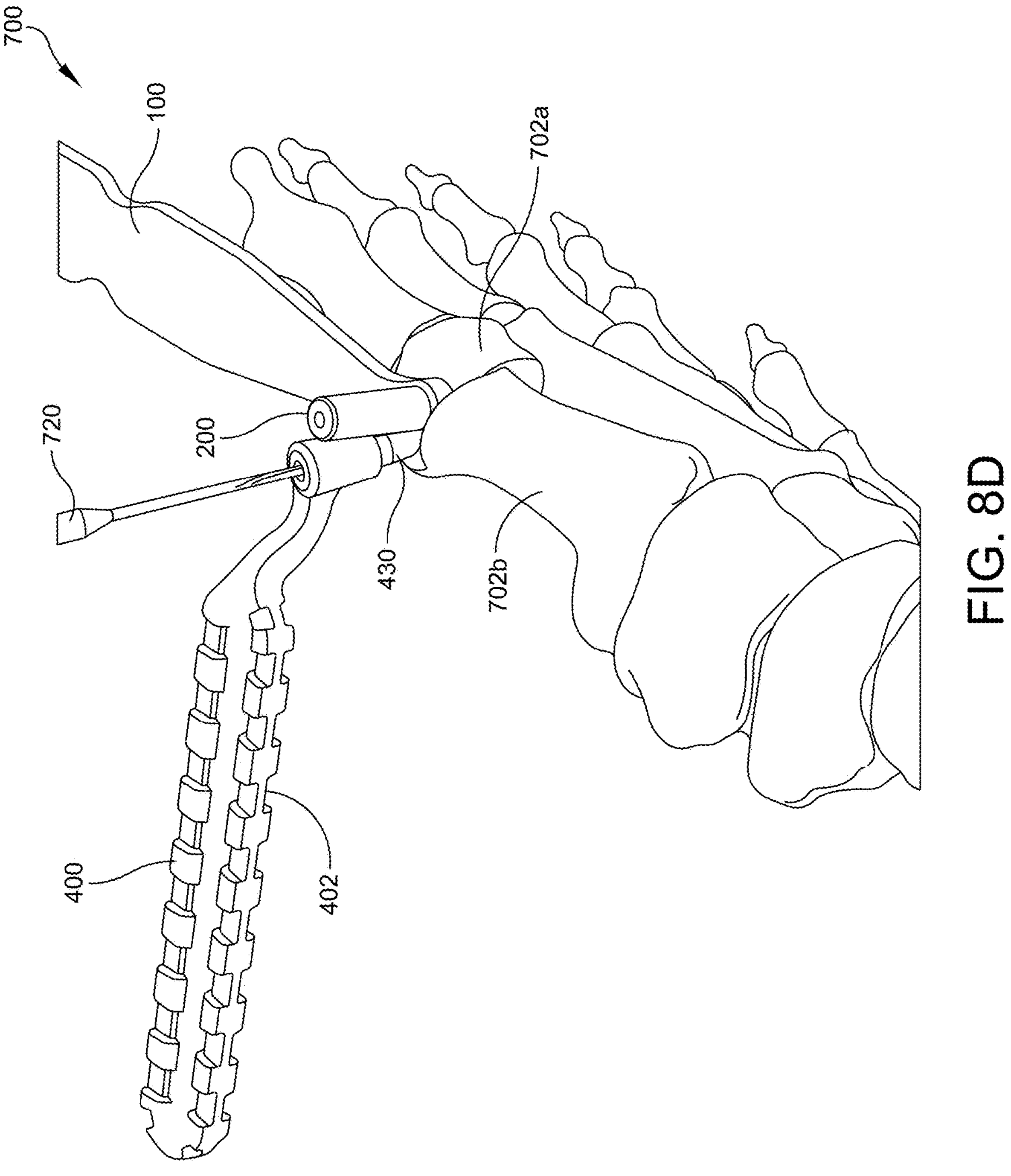
FIG. 8D illustrates a step of forming a first screw hole in a first bone portion, in accordance with some embodiments.

At step 612, and as illustrated in FIG. 8D, a first fastener channel is formed in a first bone portion 702*a* using a drill guide 400. The drill guide 400 includes a handle portion 402 and a drill guide insert 430 positioned within a head portion 404 of the drill guide. The drill guide insert 430 is configured to be at least partially inserted into the first locking aperture 40*a* formed in the ISO plate 2. The drill guide insert 430 defines a guide channel 432 sized and configured to receive a drill bit 720 therethrough. The drill bit 720 is inserted through the guide channel 432 and rotated to form a first fastener channel in the first bone portion 702*a*.

Figure 8E:
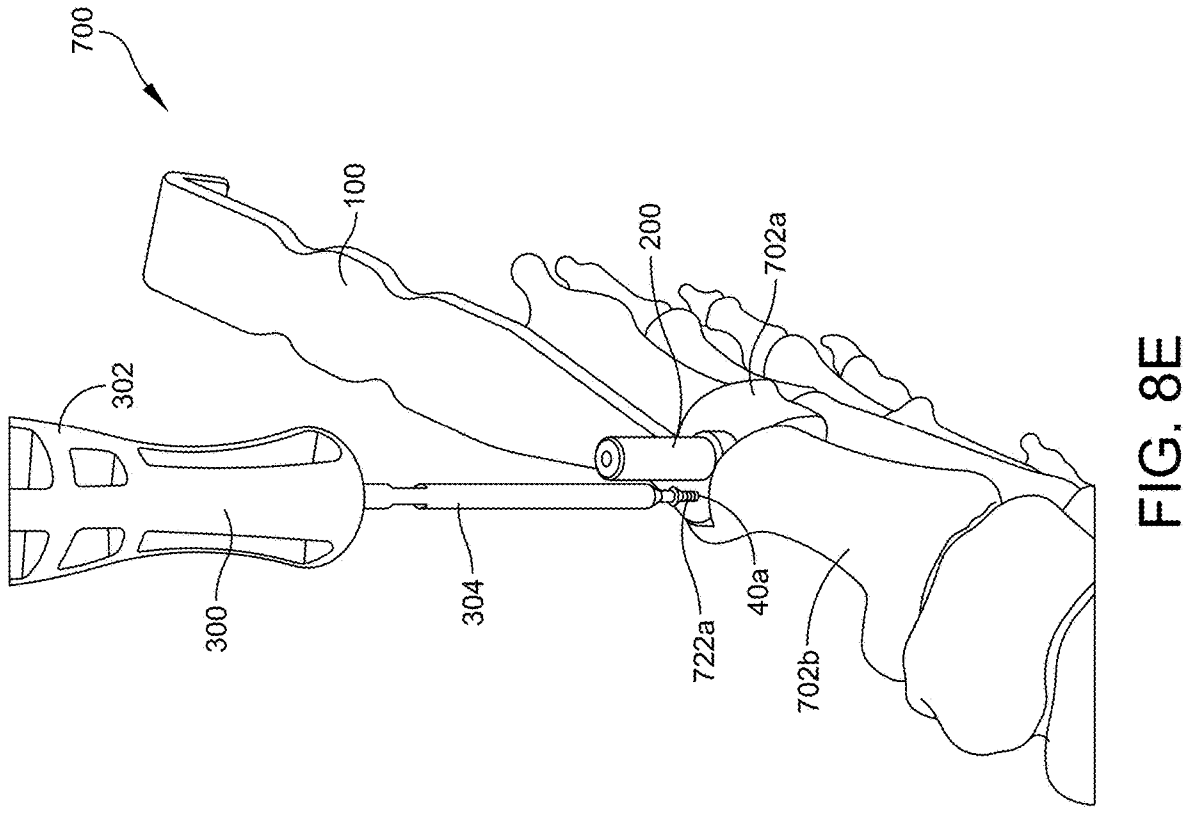
FIG. 8E illustrates a step of coupling the ISO plate to the first bone portion using a first screw, in accordance with some embodiments.

At step 614, a first locking fastener 722*a* is inserted through the first locking aperture 40*a* and into the first fastener channel in the first bone portion 702*a* to couple the ISO plate 2 to the first bone portion 702*a*. The first locking fastener 722*a* can be inserted using any suitable driver, such as, for example, the driver 300 discussed above. The driver 300 includes a driver insert 304 (or bit) configured to be received within a slot defined in the head of the first locking fastener 722*a* to drive the first locking fastener into the first fastener channel in the first bone portion 702*a* and to drive the head of the first locking fastener 722*a* into a locked engagement with the first locking aperture 40*a* defined in the ISO plate 2, as shown in FIG. 8E.

Figure 8F:
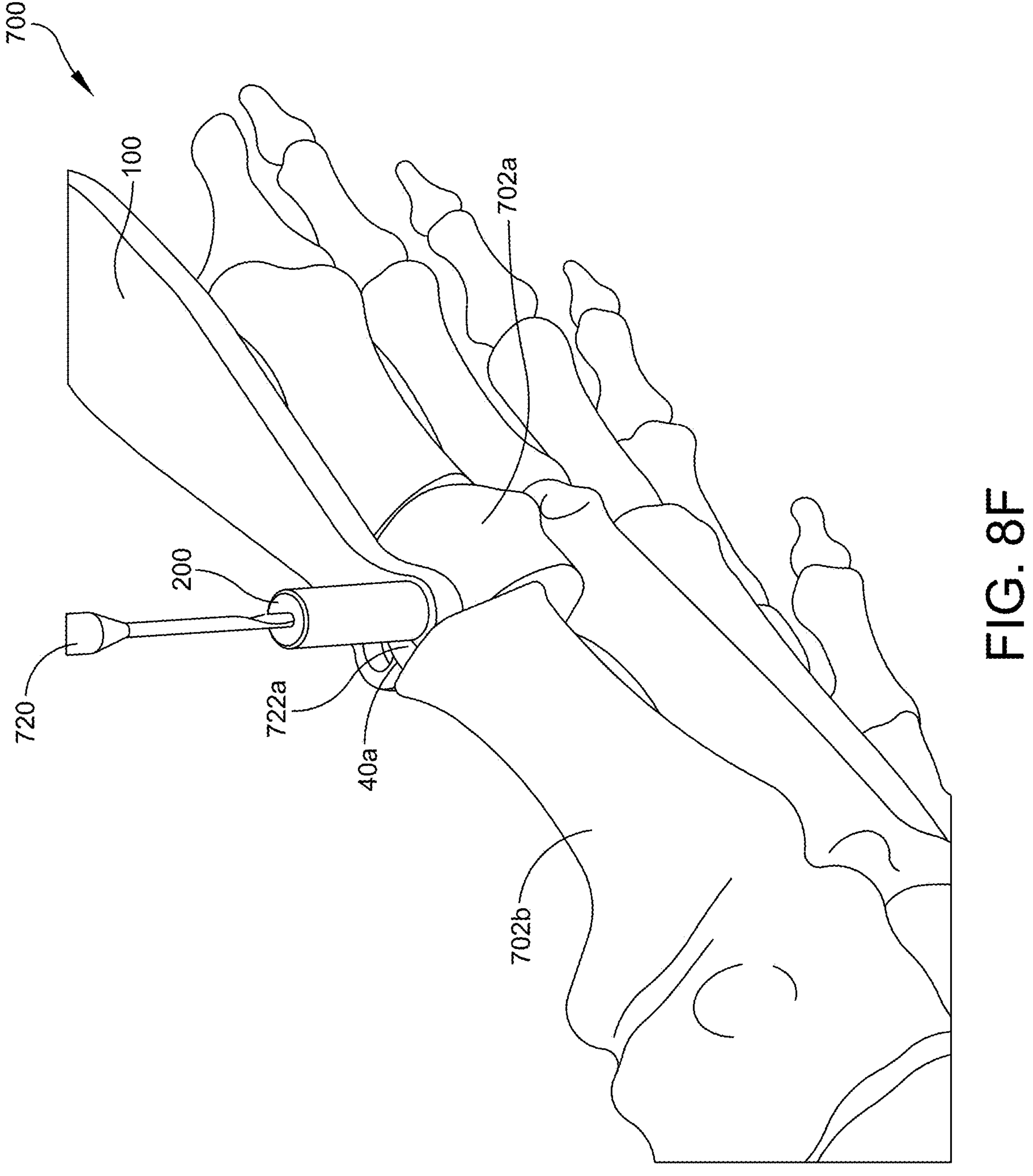
FIG. 8F illustrates a step of forming a second screw hole in a first bone portion, in accordance with some embodiments.

At step 616, and as illustrated in FIG. 8F, a second fastener channel is formed in the first bone portion 702*a*, in accordance with some embodiments. The drill bit 720 is inserted through the guide channel 208 defined in the locking drill guide 200 and rotated to form the second fastener channel in the first bone portion 702*a*. At step 618, the locking drill guide 200 is separated from the ISO plate 2 and the plate handle 100. The locking drill guide 200 and the plate handle 100 can be discarded after removal.

Figure 8G:
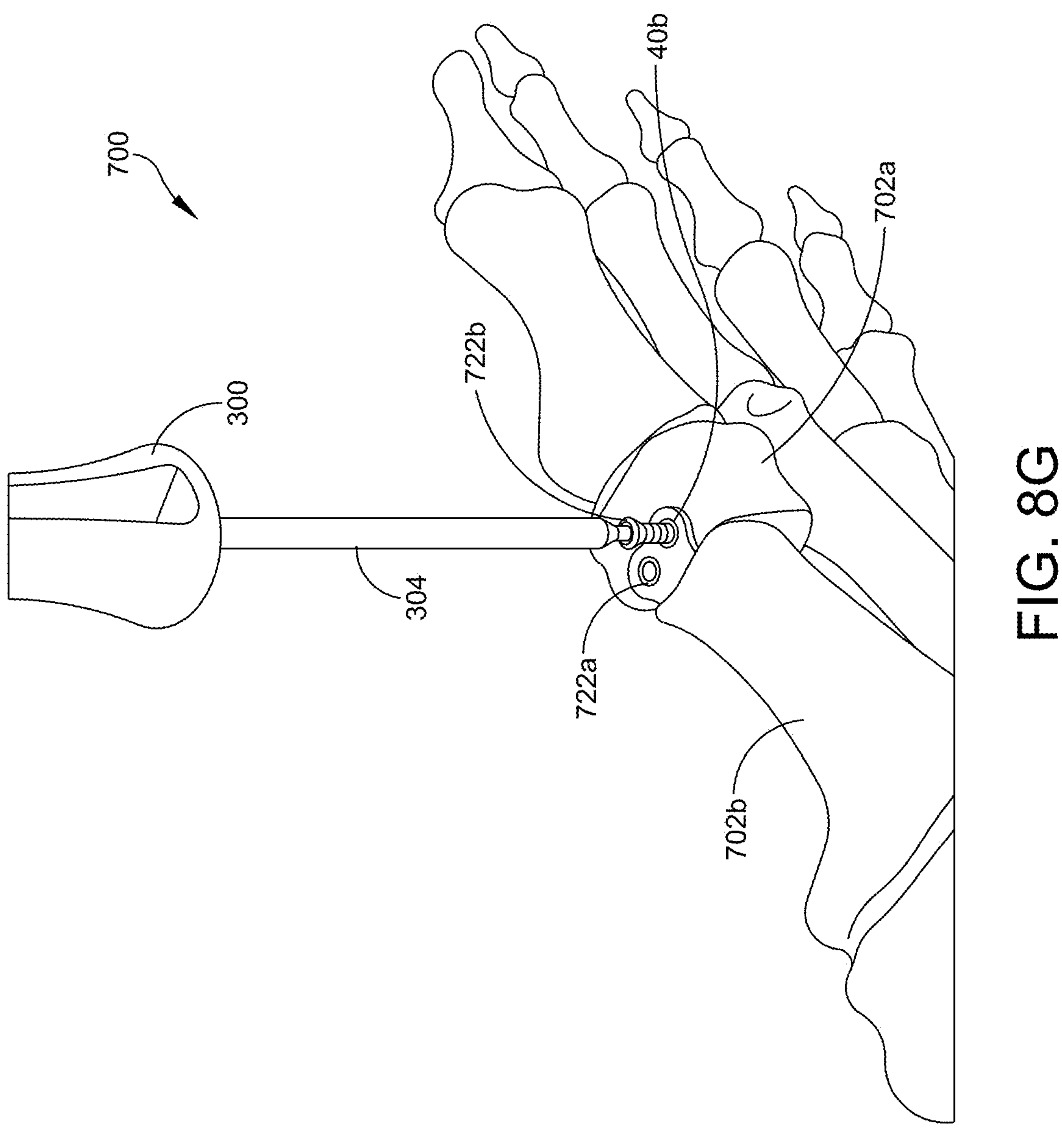
FIG. 8G illustrates a step of coupling the ISO plate to the second bone portion using a second screw, in accordance with some embodiments.

At step 620, and as illustrated in FIG. 8G, a second locking fastener is inserted through the second locking aperture 40*b* and into the second fastener channel in the first bone portion 702*a*. The second locking fastener 722*b* can be inserted using any suitable driver, such as, for example, the driver 300 discussed above. The driver 300 insert 304 is configured to be received within a slot defined in the head of the second locking fastener 722*b* to drive the second locking fastener into the second fastener channel in the first bone portion 702*a* and to drive the head of the second locking fastener 722*b* into a locked engagement with the second locking aperture 40*b* defined in the ISO plate 2.

Figure 8H:
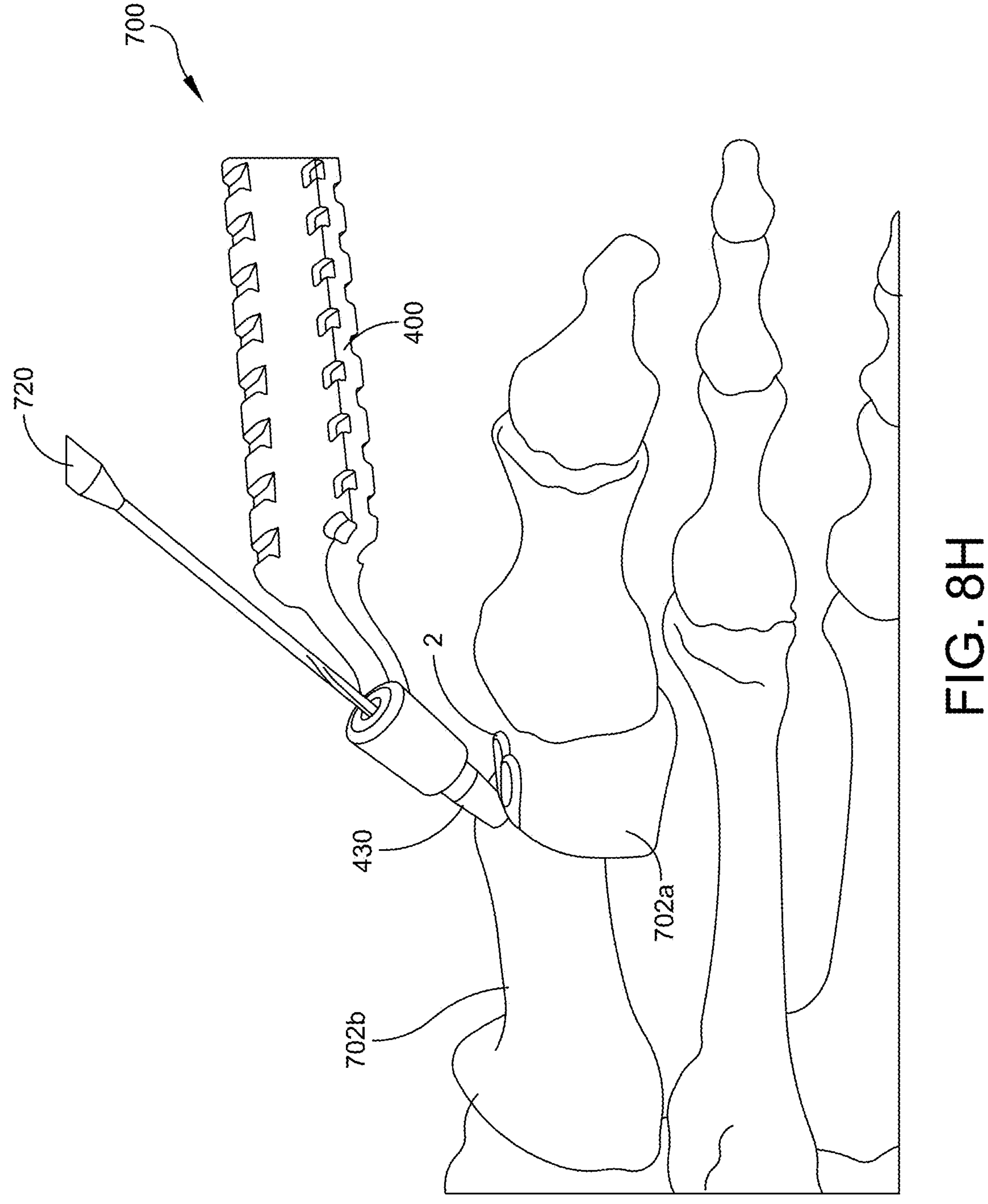
FIG. 8H illustrates a step of forming a screw hole in a second bone portion, in accordance with some embodiments.

At step 622, and as illustrated in FIG. 8H, a fastener channel is formed in the second bone portion using the drill guide 400. The drill guide insert 430 is configured to be at least partially inserted into the non-locking aperture 30 formed in the ISO plate 2. The drill guide insert 430 defines a guide channel 432 sized and configured to receive a drill bit 720 therethrough. The drill bit 720 is inserted through the guide channel 432 and rotated to form a fastener channel in the second bone portion 702*b*.

Figure 8I:
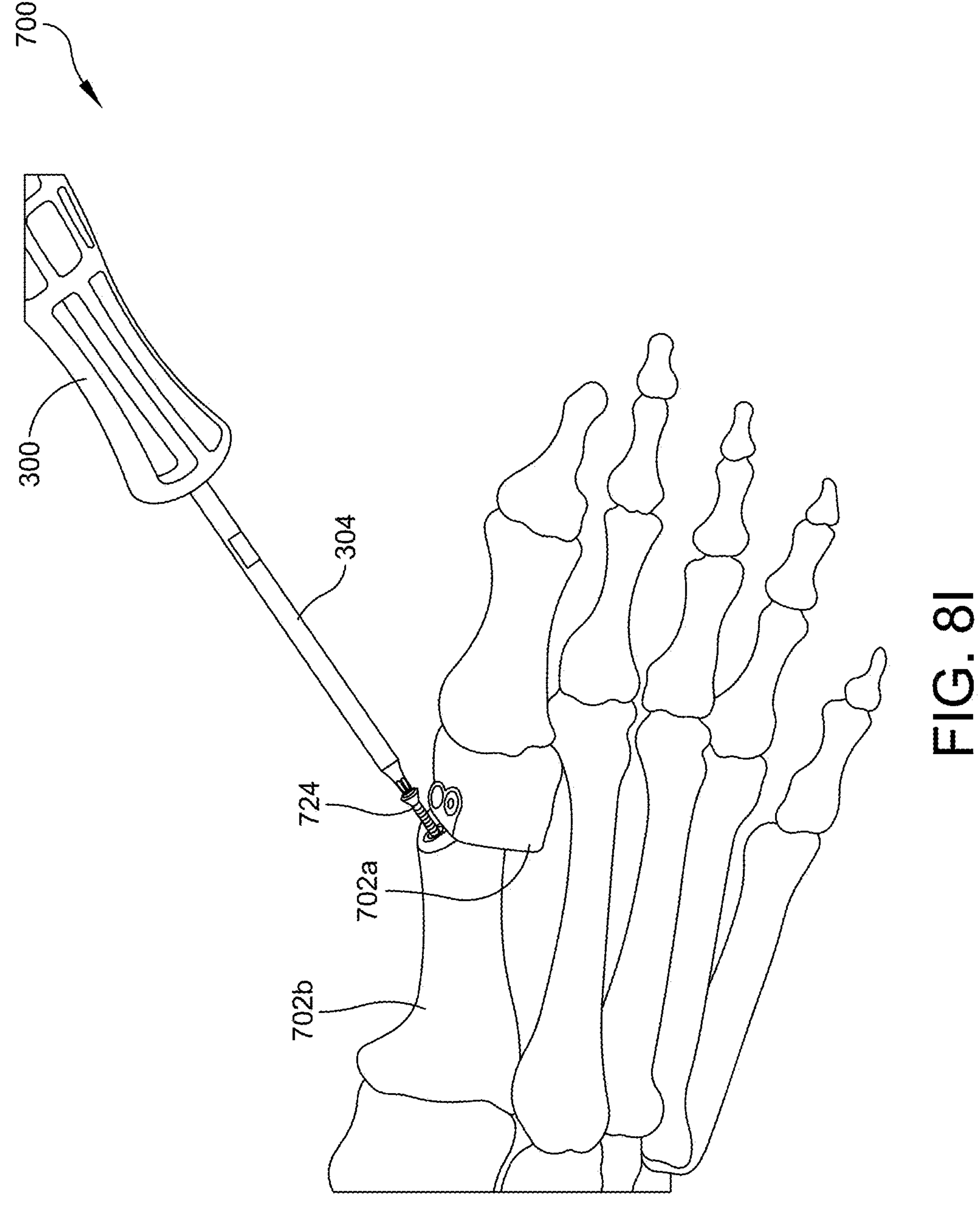
FIG. 8I illustrates a step of inserting a compression screw into a second bone portion, in accordance with some embodiments.

At step 624, and as illustrated in FIG. 8I, a non-locking fastener 724 is inserted through the non-locking fastener aperture 30 in the ISO plate 2 and into the fastener channel formed in the second bone portion 702*b*. The non-locking fastener 724 is advanced to fix the position of the second bone portion 702*b* with respect to the first bone portion 702*a*. In some embodiments, the non-locking fastener 724 is a compression fastener configured to compress the second bone portion 702*b* relative to the first bone portion 702*a*.

Figure 9B:
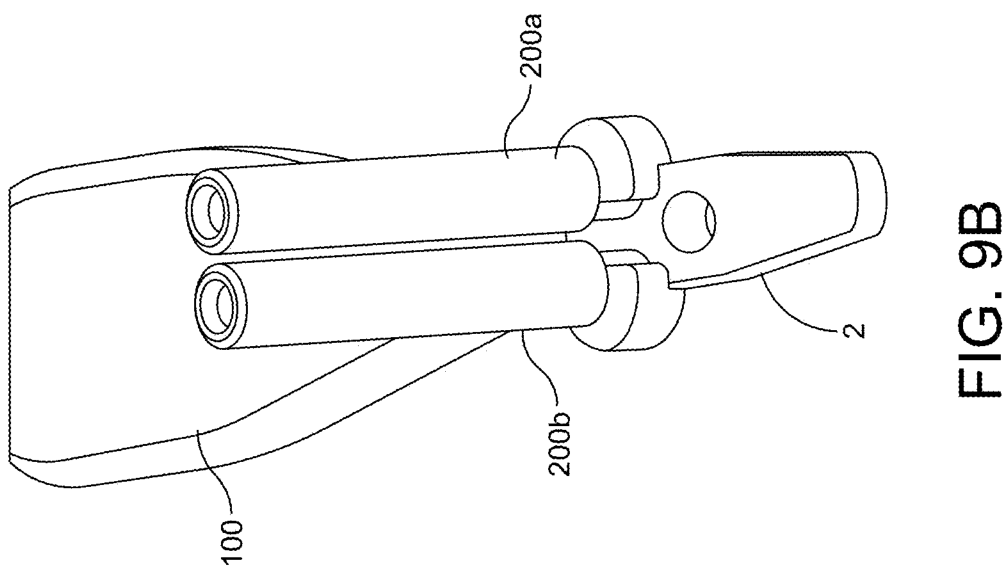
FIG. 9B illustrates a front perspective view of the plate handle of FIG. 9A, in accordance with some embodiments.
Figure 9A:
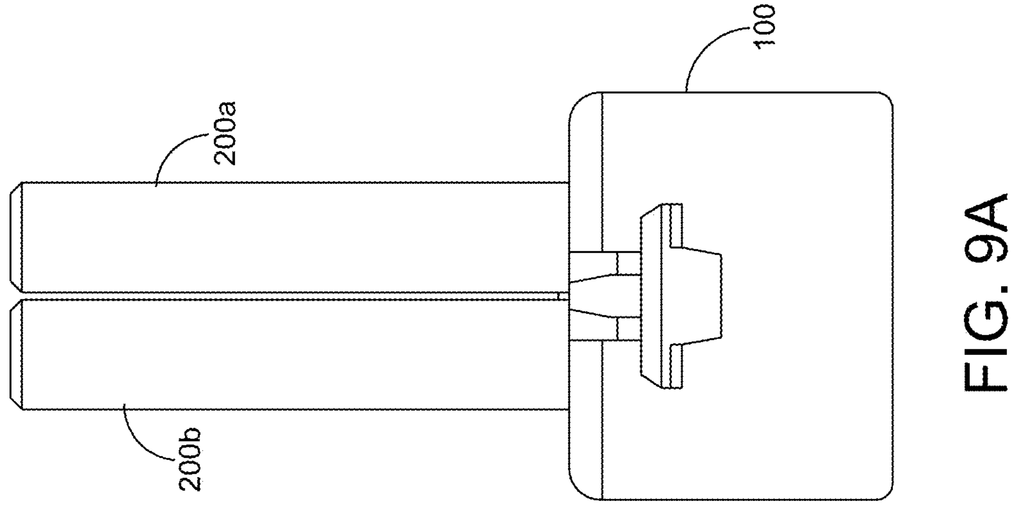
FIG. 9A illustrates a front view of a plate handle coupled to an ISO plate using a first a locking drill guide and a second locking drill guide, in accordance with some embodiments.
Figure 9C:
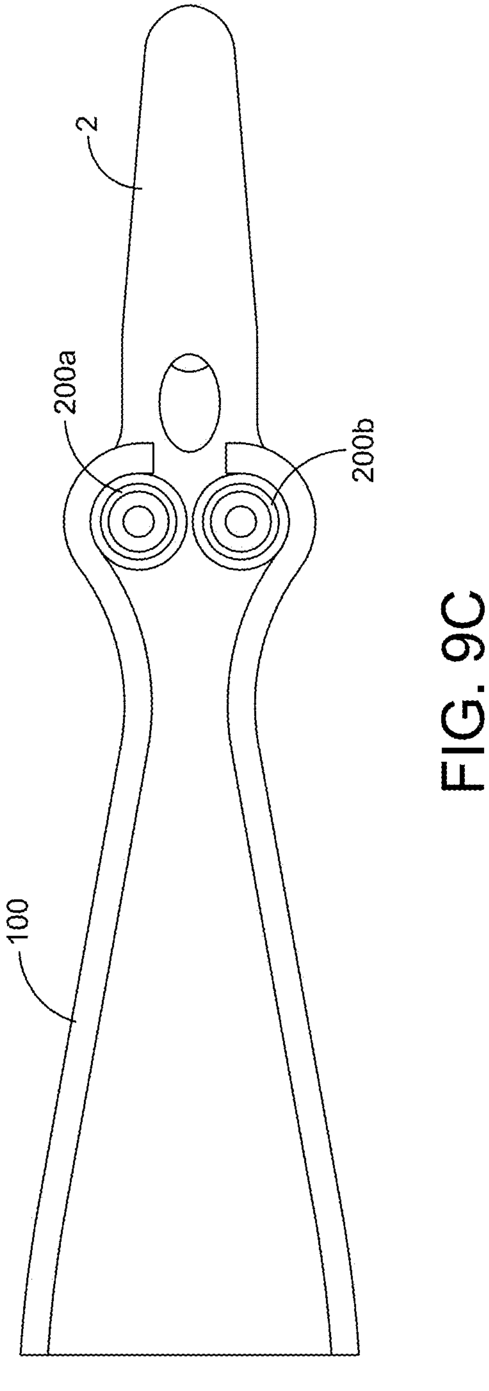
FIG. 9C illustrates a side view of the plate handle of FIG. 9A, in accordance with some embodiments.

FIGS. 9A-9C illustrate a plate handle 100 coupled to an ISO plate 2 by a first locking drill guide 200*a* and a second locking drill guide 200*b*, in accordance with some embodiments. The locking drill guides 200*a*, 200*b* are similar to the locking drill guide 200 described above, and similar description is not repeated herein. The use of two locking drill guides 200*a*, 200*b* allows each of the fastener channels to be formed in the second bone portion without using a drill guide 400. For example, in various embodiments, a first fastener hole can be formed by inserting a drill through the first locking drill guide 200*a* and a second fastener hole can be formed by inserting the drill through a second locking drill guide 200*b*. The first and/or second locking drill guides 200*a* can be removed and fasteners can be inserted through the ISO plate 2 and into the second bone portion. The removal of each of the locking drill guides 200*a*, 200*b* and insertion of a respective fastener can be performed sequentially and/or simultaneously.

Figure 10:
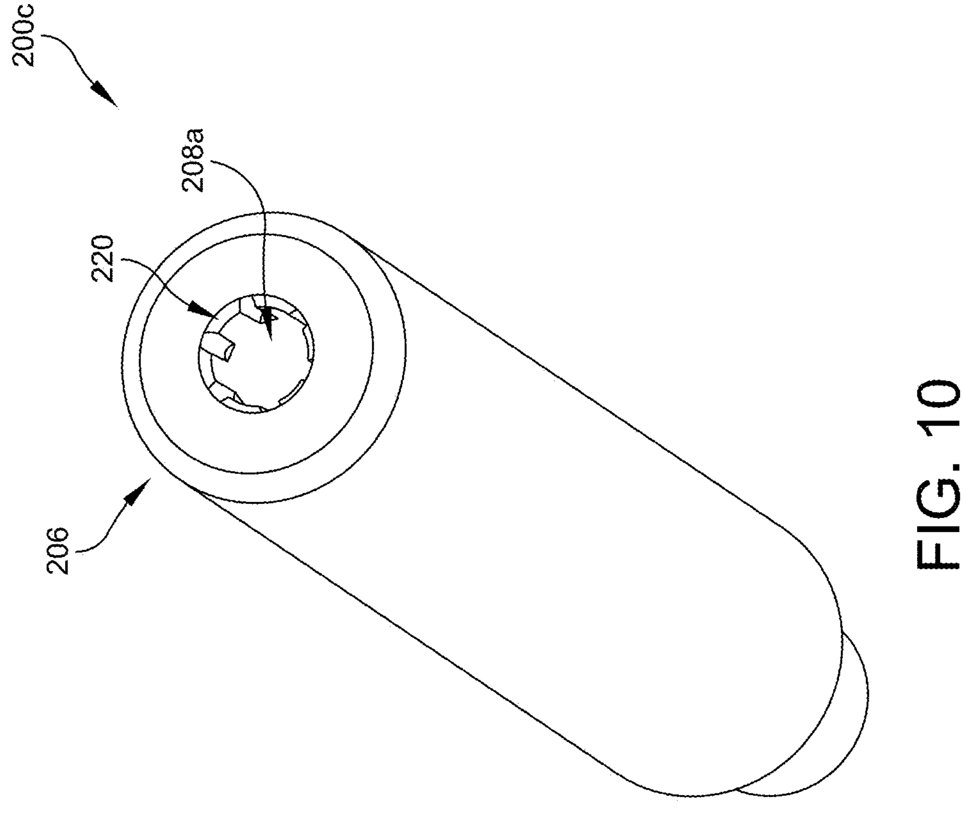
FIG. 10 illustrates a top perspective view of a locking drill guide, in accordance with some embodiments.

FIG. 10 illustrates a locking drill guide 200*c* having a channel 208*a* defining at least a partial torx cross-section configured to receive a torx driver therein, in accordance with some embodiments. The locking drill guide 200*c* is similar to the locking drill guide 200 discussed above, and similar description is not repeated herein. In the illustrated embodiment, an opening 220 is defined at the first end 206 of the locking drill guide 200*c*. The opening 220 defines a first end of the channel 208*a* and further defines a torx cross-section configured to interface with a torx-driver (not shown) inserted at least partially into the channel 208*a*. In some embodiments, the entire channel 208*a* defines a torx cross-section, although it will be appreciated that only the opening 220 and/or a portion of the channel 208*a* can define the torx cross-section. Although specific embodiments are discussed herein, it will be appreciated that the opening 220 and/or the channel 208*a* can have any suitable cross-sectional shape.

Although the subject matter has been described in terms of exemplary embodiments, it is not limited thereto. Rather, the appended claims should be construed broadly, to include other variants and embodiments, which may be made by those skilled in the art.

The invention claimed is:

1. A system, comprising:

an intraosseous sliding osteotomy (ISO) plate including:

a body extending between a first surface and a second surface and defined by a perimeter wall;

an insertion portion defining a portion of the body that is sized and configured to insert into a medullary canal of a bone, the insertion portion including a tapered portion having a width extending between the perimeter wall that increases from the first end to a first position in the body;

a compression portion including a non-locking fastener aperture that extends through the body at a predetermined angle;

a fixation portion extending from a second position in the body to the second end and including a plurality of fastener apertures adjacent to each other laterally across a width of the body and extending from the first surface to the second surface; and a plate handle configured to be coupled to the ISO plate and including a handle head positioned at a distal end of a handle body, wherein the handle head includes an opening configured to receive at least one locking drill guide and defined by a first circular portion, a second circular portion, and a channel extending from the first and the second circular portions to a distal edge of the handle body.

2. The system of claim 1, wherein the ISO plate further includes a shroud extending from the second surface and defining a portion of the non-locking fastener aperture.

3. The system of claim 2, wherein the shroud is configured to receive a non-locking screw such that when the non-locking screw is inserted through the non-locking fastener aperture, a head of the non-locking screw is contained entirely within the shroud.

4. The system of claim 1, wherein the insertion portion includes a leading edge tapered between the first surface and the second surface.

5. The system of claim 1, wherein the plurality of fastener apertures are locking fastenings apertures that are each configured to receive a locking fastener.

6. The system of claim 1, further comprising a locking drill guide configured to couple the ISO plate to a plate handle, wherein the locking drill guide includes:

a body defining a channel extending therethrough from a first end to a second end and extending parallel to a longitudinal axis of the body, the channel being configured to interface with a driver inserted into the channel, a locking extension extending from the first end and including at least one locking feature configured to couple the locking drill guide to the ISO plate via at least one of the plurality of fastener apertures, and a handle contact edge defined at the first end and sized and configured to contact a surface of a head of the plate handle and lock the locking drill guide to the ISO plate while compressing the head of the plate handle between the locking drill guide and the ISO plate.

7. The system of claim 1, further comprising a drill guide configured to guide formation of a channel in a bone, wherein:

the drill guide includes a head portion coupled to a distal end of a handle portion, the head portion includes a neck extending from the handle portion and an insert receiving portion, the neck includes an offset portion that extends a predetermined distance to position the insert receiving portion at a predetermined vertical offset from the handle portion, and the insert receiving portion includes a body defining an insert channel extending therethrough and configured to receive a drill guide insert therein.

8. The system of claim 7, further comprising a drill guide insert, wherein:

the drill guide insert includes a substantially cylindrical body including a tapered insert portion and a guide channel extending through the cylindrical body that is configured to receive a drill bit therethrough for drilling into a bone, and the drill guide insert is sized and configured to be received within the insert channel such that a central longitudinal axis of the insert channel and a central longitudinal axis of the cylindrical body are aligned.

9. The system of claim 8, wherein the drill guide insert is sized and configured to be inserted into one of the plurality of fastener apertures and/or the non-locking fastener aperture of the ISO plate.

10. The system of claim 1, further comprising a broach including a broach insert coupled to a broach handle, wherein the broach handle defines a channel sized and configured to receive a portion of the broach insert therein, the broach insert comprises an insertion portion having a first thickness and a coupling portion having a second thickness, and the first thickness is less than the second thickness.

11. A method of forming an osteotomy, comprising:

cutting a bone to define a first bone portion and a second bone portion;

inserting a broach partially into a cut in the bone;

rotating the broach to displace the first bone portion from the second bone portion;

partially inserting an intraosseous sliding osteotomy (ISO) plate having a tapered leading edge into the second bone portion;

forming a first fastener channel in the first bone portion using a drill guide including a drill guide insert positioned within a head portion of the drill guide by inserting the drill guide insert into a first locking aperture of the ISO plate and drilling through the drill guide insert;

inserting a first locking fastener through the first locking aperture and into the first fastener channel;

forming a second fastener channel in the second bone portion using the drill guide insert by inserting the drill guide insert into a non-locking aperture of the ISO plate and drilling through the drill guide insert; and inserting a non-locking fastener through the non-locking aperture and into the second fastener channel.

12. The method of claim 11 further comprising, inserting a k-wire into the first bone portion to keep the first bone portion from shifting with respect to the second bone portion.

13. The method of claim 11 further comprising, defining a cavity in the second bone portion using the broach.

14. The method of claim 11 further comprising, forming a third fastener channel in the first bone portion using the drill guide and the drill guide insert by inserting the drill guide insert into a second locking aperture of the ISO plate and drilling through the drill guide insert; and inserting a second locking fastener through the second locking aperture and into the third fastener channel.

15. The method of claim 11 further comprising, coupling a plate handle to the ISO plate using the drill guide.

16. The method of claim 15, wherein the drill guide is a locking drill guide including a locking extension that extends through a portion of an opening formed in the plate handle that is coupled to the first locking aperture, and the locking drill guide locks the plate handle and the ISO plate in a fixed engagement and transfers a force applied to the plate handle to the ISO plate.

17. The method of claim 11, wherein the drill guide includes a first locking drill guide and a second locking drill guide such that the first fastener channel is defined using the first locking drill guide and a third fastener channel in the first bone portion is defined using the second locking drill guide.

18. The method of claim 11, wherein the non-locking fastener is a compression fastener configured to compress the second bone portion relative to the first bone portion.

19. The method of claim 11, wherein the drill guide includes a channel defining a partial torx cross-section configured to receive a torx driver.

20. A system, comprising:

an intraosseous sliding osteotomy (ISO) plate including a non-locking fastener aperture that extends through the body at a predetermined angle, a fixation portion extending from a second position in the body to the second end and including a plurality of fastener apertures adjacent to each other laterally across a width of the body and extending from the first surface to the second surface; and a drill guide including a head portion including a neck extending from a handle portion and an insert receiving portion sized and configured to be inserted into any one of the non-locking fastener aperture and fastener apertures of the ISO plate, wherein the neck includes an offset portion that extends a predetermined distance to position the insert receiving portion at a predetermined vertical offset from the handle portion, and the insert receiving portion includes a body defining an insert channel extending therethrough and configured to receive a drill guide insert therein.

21. The system of claim 20, wherein the drill guide insert includes a substantially cylindrical body including a tapered insert portion and a guide channel extending through the cylindrical body that is configured to receive a drill bit therethrough for drilling into a bone.

22. The system of claim 20, wherein the drill guide insert includes a substantially cylindrical body, and the drill guide insert is sized and configured to be received within the insert channel such that a central longitudinal axis of the insert channel and a central longitudinal axis of the cylindrical body are aligned.

23. The system of claim 20, wherein the drill guide insert is sized and configured to be inserted into the fastener aperture of the ISO plate.

24. The system of claim 20, further comprising a plate handle configured to be coupled to the ISO plate via the fastener aperture and including a handle head positioned at a distal end of a body, wherein the handle head includes a body having an opening configured to receive at least one locking drill guide and defined by a first circular portion, a second circular portion, and a channel extending from the first and the second circular portions to a distal edge of the body.

25. The system of claim 20, further comprising a broach including a broach insert coupled to a broach handle, the broach insert including an insertion portion having a first thickness and a coupling portion having a second thickness, and the first thickness is less than the second thickness.

* * * * *